(12) United States Patent
Daems et al.

(10) Patent No.: US 11,614,403 B2
(45) Date of Patent: Mar. 28, 2023

(54) NUCLEIC ACID ENZYME SENSOR

(71) Applicant: FOx Biosystems NV, Diepenbeek (BE)

(72) Inventors: Devin Daems, Boom (BE); Filip Delport, Temse (BE); Jeroen Lammertyn, Neerijse (BE); Bernd Peeters, Turnhout (BE)

(73) Assignee: FOX BIOSYSTEMS NV, Temse (BE)

( * ) Notice: Subject to any disclaimer, the term of this patent is extended or adjusted under 35 U.S.C. 154(b) by 495 days.

(21) Appl. No.: 16/645,170

(22) PCT Filed: Aug. 10, 2018

(86) PCT No.: PCT/EP2018/071764
§ 371 (c)(1),
(2) Date: Mar. 6, 2020

(87) PCT Pub. No.: WO2019/030383
PCT Pub. Date: Feb. 14, 2019

(65) Prior Publication Data
US 2021/0080392 A1    Mar. 18, 2021

Related U.S. Application Data

(60) Provisional application No. 62/543,802, filed on Aug. 10, 2017.

(51) Int. Cl.
*G01N 21/552* (2014.01)
*C12Q 1/6825* (2018.01)
*B82Y 35/00* (2011.01)

(52) U.S. Cl.
CPC ......... *G01N 21/554* (2013.01); *C12Q 1/6825* (2013.01); *B82Y 35/00* (2013.01); *C12Q 2521/345* (2013.01)

(58) Field of Classification Search
CPC .... G01N 21/554; B82Y 35/00; C12Q 1/6825; C12Q 2521/345; C12Q 2565/628
See application file for complete search history.

(56) References Cited

U.S. PATENT DOCUMENTS

| | | |
|---|---|---|
| 2006/0211024 A1 | 9/2006 | Corn et al. |
| 2009/0155785 A1* | 6/2009 | Mirkin ..................... B82Y 5/00 435/6.12 |
| 2010/0047789 A1* | 2/2010 | Chen ..................... G01N 21/553 435/6.16 |
| 2010/0105039 A1 | 4/2010 | Lu et al. |
| 2016/0108465 A1* | 4/2016 | Chan ..................... C12Q 1/6823 506/9 |

FOREIGN PATENT DOCUMENTS

| | | |
|---|---|---|
| EP | 2817421 A1 | 12/2014 |
| WO | 03100077 A2 | 12/2003 |

OTHER PUBLICATIONS

Peeters et al, Real-Time FO-SPR Monitoring of Solid-Phase DNAzyme Cleavage Activity for Cutting-Edge Biosensing, 2019, ACS Appl. Mater. Interfaces, 11, 6759-6768. (Year: 2019).*
Breaker, et al., "A DNA enzyme that cleaves RNA," Chemistry and Molecular Biology, 1994, 1, 223-229.
Santoro, et al., "A general purpose RNA-cleaving DNA enzyme," Proc. Natl. Acad. Sci. USA, 1997, 94 (9), 4262-4266.
Yurke, et al., "A DNA-fuelled molecular machine made of DNA," Nature, 2000, 406 (6796), 605-608.
Markham, et al., "DINAMelt web server for nucleic acid melting prediction," Nucleic Acids Research, 2005, 33 (Web Server issue), W577-W581.
Markham, N. R. and Zuker, M., "UNAFold: software for nucleic acid folding and hybridization," Methods in Molecular Biology, 2008, 3-31.
Boersma, et al., "Enantioselective Friedel-Crafts Reactions in Water Using a DNA-Based Catalyst," Angew. Chem. Int. Ed., vol. 48, No. 18, pp. 3346-3348, 2009.
Pollet, , et al., "Fiber optic SPR biosensing of DNA hybridization and DNA-protein interaction," Biosensors and Bioelectronics, 2009, 25 (4), 864-869.
Mokany, et al., "MNAzymes, a Versatile New Class of Nucleic Acid Enzymes That Can Function as Biosensors and Molecular Switches," Journal of the American Chemical Society, vol. 132, No. 3. pp. 1051-1059, Jan. 2010.
J. Kosman and B. Juskowiak, "Peroxidase-mimicking DNAzymes for biosensing applications: A review," Analytica Chimica Acta, vol. 707, No. 1, pp. 7-17, 2011.
Knez, et al., "Fiber-Optick High Resolution Genetic Screening using Gold-Labeled Gene Probes," J. Small, 2012, 8 (6), 868-872.
Malinsky, , et al., "Early stages of growth of gold layers sputter deposited on glass and silicon substrates," Nanoscale Research Letters, 2012, 7 (1), 241.
Bone, et al., "DNAzyme switches for molecular computation and signal amplification," Biosensors and Bioelectronics, 2015, 70, 330-337.

(Continued)

*Primary Examiner* — Narayan K Bhat
(74) *Attorney, Agent, or Firm* — Dinsmore & Shohl, LLP

(57) ABSTRACT

NAzyme activity surface plasmon resonance sensors include a first DNA probe that is covalently connected to a sensing surface, and a second DNA probe that is covalently connected to a nanoparticle or a nanoparticle cluster. The first DNA probe and the second DNA probe are ligated together to provide a selected single strand DNA probe connected to the sensing surface and the nanoparticle. The single strand DNA probe includes a ligation zone within a selected NAzyme substrate. The sensor measures DNAzyme activity by NAzyme binding at the NAzyme substrate and cleavage at the ligation zone. Fiber optic surface plasmon resonance sensor tips are adapted to measure activity of a NAzyme when the NAzyme substrate is recognized by the selected NAzyme through hybridization and the metallic nanoparticle is released from the sensor by cleavage of the single strand DNA at the ligation zone by the selected NAzyme.

14 Claims, 19 Drawing Sheets

Specification includes a Sequence Listing.

(56) References Cited

OTHER PUBLICATIONS

Knez, , et al., "Real-time ligation chain reaction for DNA quantification and identification on the FO-SPR," Biosensors Bioelectronics, 2014, 67, 394-399.
Lu, et al., "Fiber optic—SPR platform for fast and sensitive infliximab detection in serum of inflammatory bowel disease patients," Biosensors and Bioelectronics, 2016, 79, 173-179.
Daems, , et al., "Competitive inhibition assay for the detection of progesterone in dairy milk using a fiber optic SPR biosensor," Analytica Chimica Acta, 2017, 950, 1-6.
International Search Report dated Sep. 26, 2018 in related International Patent Application No. PCT/EP2018/071764.
International Preliminary Report on Patentability dated Feb. 11, 2020 in related International Patent Application No. PCT/EP2018/071764.

* cited by examiner

* RNA base

SEQUENCE LISTING

```
<160> NUMBER OF SEQ ID NOS: 10

<210> SEQ ID NO 1
<211> LENGTH: 31
<212> TYPE: DNA
<213> ORGANISM: artificial
<220> FEATURE:
<223> OTHER INFORMATION: FO-SPR sensor immobilized chimeric DNA/RNA
      strand or sequence containing the full substrate strand or
      sequence for nucleic acid enzymes; to be covalently coupled with
      the particle immobilized strand or sequence (3)
<220> FEATURE:
<221> NAME/KEY: misc_feature
<222> LOCATION: (11)..(11)
<223> OTHER INFORMATION: n is a derivative of guanine with ribose
<220> FEATURE:
<221> NAME/KEY: misc_feature
<222> LOCATION: (12)..(12)
<223> OTHER INFORMATION: n is a derivative of uracil with ribose

<400> SEQUENCE: 1
cagcacaacc nncaccaacc gttttttttt t                                    31

<210> SEQ ID NO 2
<211> LENGTH: 31
<212> TYPE: DNA
<213> ORGANISM: artificial
<220> FEATURE:
<223> OTHER INFORMATION: FO-SPR sensor immobilized chimeric DNA/RNA
      strand or sequence containing the full substrate strand or
      sequence for nucleic acid enzymes; to be covalently coupled with
      the particle immobilized strand or sequence (3)
<220> FEATURE:
<221> NAME/KEY: misc_feature
<222> LOCATION: (11)..(11)
<223> OTHER INFORMATION: n is a derivative of guanine with ribose
<220> FEATURE:
<221> NAME/KEY: misc_feature
<222> LOCATION: (12)..(12)
<223> OTHER INFORMATION: n is a derivative of uracil with ribose

<400> SEQUENCE: 2
cagcacaacc nncaccaacc gcattttttt t                                    31

<210> SEQ ID NO 3
<211> LENGTH: 25
<212> TYPE: DNA
<213> ORGANISM: artificial
<220> FEATURE:
<223> OTHER INFORMATION: particle immobilized strand or sequence to
      label the substrate strand or sequence (1) or (2)
```

-continued

<400> SEQUENCE: 3
tttttttttt gagggattat tgtta                                                25

<210> SEQ ID NO 4
<211> LENGTH: 25
<212> TYPE: DNA
<213> ORGANISM: artificial
<220> FEATURE:
<223> OTHER INFORMATION: ligation template strand or sequence to align
      the particle immobilized strand or sequence (3) and FO-SPR sensor
      immobilized strand or sequence (1) or (2) to enable covalent
      coupling through ligation

<400> SEQUENCE: 4
ggttgtgctg taacaataat ccctc                                                25

<210> SEQ ID NO 5
<211> LENGTH: 33
<212> TYPE: DNA
<213> ORGANISM: artificial
<220> FEATURE:
<223> OTHER INFORMATION: FO-SPR sensor immobilized strand or sequence
      containing part of the substrate strand or sequence; full
      substrate strand or sequence for nucleic acid enzymes only formed
      after ligation with particle immobilized strand or sequence (6)

<400> SEQUENCE: 5
tttttttttt gagggattat agtatcagca caa                                       33

<210> SEQ ID NO 6
<211> LENGTH: 23
<212> TYPE: DNA
<213> ORGANISM: artificial
<220> FEATURE:
<223> OTHER INFORMATION: particle immobilized chimeric DNA/RNA strand or
      sequence containing part of the substrate strand or sequence;full
      substrate strand or sequence for nucleic acids enzymes only
      formed after ligation with FO-SPR immobilized strand or
<220> FEATURE:
<221> NAME/KEY: misc_feature
<222> LOCATION: (3)..(3)
<223> OTHER INFORMATION: derivative of guanine with ribose
<220> FEATURE:
<221> NAME/KEY: misc_feature
<222> LOCATION: (4)..(4)
<223> OTHER INFORMATION: derivative of uracil with ribose
<220> FEATURE:
<221> NAME/KEY: misc_feature
<222> LOCATION: (4)..(4)
<223> OTHER INFORMATION: n is a derivative of uracil with ribose

<400> SEQUENCE: 6
ccnncaccaa ccgttttttt ttt                                                  23

<210> SEQ ID NO 7
<211> LENGTH: 24
<212> TYPE: DNA
<213> ORGANISM: artificial
<220> FEATURE:
<223> OTHER INFORMATION: ligation template strand or sequence to align
      the particle immobilized strand or sequence (6) and FO-SPR
      immobilized strand or sequence (5) to enable covalent coupling
      through ligation

<400> SEQUENCE: 7
ttggtgacgg ttgtgctgat acta                                                 24

<210> SEQ ID NO 8

```
<211> LENGTH: 35
<212> TYPE: DNA
<213> ORGANISM: artificial
<220> FEATURE:
<223> OTHER INFORMATION: nucleic acid enzyme or 10-23 DNAzyme

<400> SEQUENCE: 8
cggttggtga ggctagctac aacgaggttg tgctg                              35

<210> SEQ ID NO 9
<211> LENGTH: 52
<212> TYPE: DNA
<213> ORGANISM: artificial
<220> FEATURE:
<223> OTHER INFORMATION: Inhibitor strand or sequence to temporarily
      block the DNAzyme strand or sequence (8) for controlled DNAzyme
      activity

<400> SEQUENCE: 9
cagcgcaacc tcgttgatca cgcctcgtct cctcccagta gcctcaccaa cc           52

<210> SEQ ID NO 10
<211> LENGTH: 43
<212> TYPE: DNA
<213> ORGANISM: artificial
<220> FEATURE:
<223> OTHER INFORMATION: Specific target strand or sequence able to
      recognizes and bind the inhibitor strand or sequence and
      specifically release the DNAzyme strand or sequence

<400> SEQUENCE: 10
ggtgaggcta ctgggaggag acgaggcgtg atcaacgagg ttg                     43
```

NUCLEIC ACID ENZYME SENSOR

CROSS REFERENCES TO RELATED APPLICATIONS

This application is a national-phase entry under 35 U.S.C. § 371 of International Application PCT/EP2018/071764 designating the United States, filed Aug. 10, 2018, which international application claims the benefit of priority to U.S. Provisional Application Ser. No. 62/543,802, filed Aug. 10, 2017.

BACKGROUND AND SUMMARY

Background of the Invention

A. Field of the Invention

The present invention relates generally to methods of enzyme activity measurement and sensors therefor. More particularly the invention relates to a surface plasmon resonance (SPR) sensor and method for measuring activity of nucleic acid enzymes (NAzymes) and it relates to a sensor for the direct detection of NAzyme cleavage activity. Such activity to be analysed can be for instance NAzyme, or activity of NAzymes combined with substrate of another NAzyme, for instance, NAzyme combined with substrate of another NAzyme, in a fluid and a specific biosensor for performing such methods.

An aspect of present invention is a surface plasmon resonance (SPR) real-time monitoring system of NAzyme cleavage activity manufactured by ligation of a metallic nanoparticle (NP)-labelled DNA-sequence to a DNA-sequence that is coupled directly to a SPR sensing surface (e.g. the sensing surface of a FO-SPR gold surface) or to a microcarrier or microbead, preferably a microcarrier or microbead which can be separated from a fluid and that incorporates a NAzyme selective substrate.

Furthermore, incorporation of temporary inactivating the NAzyme with an inhibitor strand or a NAzyme blocking DNA sequence, containing an internal loop for target recognition independent of the catalytic activity from the NAzyme binding arms in the SPR sensor, e.g. FO-SPR sensor, allows real-time monitoring system of NAzyme cleavage activity in function of binding of selected targets (peptides, polypeptides, protein, small molecules, nucleotides, fat groups) to the internal loop of said the inhibitor strand.

Such operational sensing system and method to manufacture are further explained in details in this application.

B. Description of the Related Art

There is an increasing need in the art for faster, cost-effective, robust, in situ analysis and personalized in vitro diagnostics. Enzyme-linked immunosorbent assay (ELISA) and high resolution melting analysis (HRM) became the gold standards for the detection of proteins and DNA respectively, as they are highly specific due to the implementation of antibodies (Abs) or complementary oligonucleotides.

ELISA-based methods, however, face some drawbacks to be dealt with: (i) extensive sample handling, (ii) the need of highly trained staff, which significantly increases costs, (iii) batch-to-batch variations of Abs and (iv) a specific adsorption of the enzymes, used for signal generation, which can lead to false positives. Similarly, High Resolution Melt (HRM) based methods combined with the polymerase chain reaction (PCR) are characterized by a higher sensitivity, but are also relatively complex, sensitive to contamination, require thermocycling and instable enzymes for target amplification.

Importantly, both for ELISA and HRM-based techniques, all assay components and steps (e.g. bioreceptor selection, surface chemistries and immobilization strategies for bioreceptors, sample preparation, signal read-out, etc.) are mostly optimized in function of a certain group of molecules (i.e. proteins, nucleic acids (NAs), small molecules, . . . ) or even in function of one particular target. Once optimized, it is very rare that an assay concept can be adapted towards another target or to be extended to a different group of molecules without re-starting the entire assay development, which makes this very timely and costly process. In addition, this particular aspect limits the diversity of applications for any given working biosensor, thereby tremendously slowing down their realization in different fields.

Thus, there is a need in the art for highly sensitive, specific and practical DNAzyme activity analysis using a generic signal generation principle which is not prone to biological and optical inhibitory effects; present invention provides such DNAzyme activity sensor.

Present invention solves these problems in the art by a universal NAzyme based technology usable to detect different types of target molecules (RNA, DNA, small molecules, peptides, etc.) and to monitor NAzyme activity. This developed NAzyme based concept catalyzes an universal substrate specifically ligated between two solid phase parts (SPR sensor or solid surfaces and nanoparticles). Using a blocked NAzyme triggered by a specific target to start the catalytic reaction, this concept can easily be adapted towards another target. Moreover this NAzyme based technology allows with its technical improvements to integrate HRM and PCR.

SUMMARY OF THE INVENTION

The present invention solves the problems of the related art by a highly sensitive sensor for sensing nucleic acid enzyme activity in a fluid.

In accordance with the purpose of the invention, as embodied and broadly described herein, the invention relates to a method of preparing a device or system for sensing NAzyme (for instance DNAzyme) activity in a fluid, whereby selective NAzyme substrates between two solid surfaces is generated. At least one of the solid surfaces is of a solid nanoparticle that is released by the NAzyme of the substrate. The system combines NAzyme initiation and amplification technology with Surface Plasmon Resonance (SPR) sensing. In one aspect of the invention, the NAzyme activity in a fluid is measured by SPR biosensor directly by release of the nanoparticle from the other solid surface or by binding of the released particle with its nucleotide sequence to a complementary nucleotide sequence on a sensing surface of a SPR sensor. By providing different NAzyme single strand nucleotide substrates that are each selective for a different NAzyme connected between the solid surface, whereof at least one of a solid nanoparticle, whereby after NAzyme cleavage each of the released particles carries a different nucleotide sequence complementary to nucleotide sequence on a SPR sensing surface, allows multiplex SPR analysis.

The technique includes: a) incubation of the fluid comprising an unknown NAzyme concentration with the SPR sensor detection zone of which the sensing surface is covered or surface coated with a mixture of substance that prevents or minimize nonspecific interaction between analyte (physical adsorption of the substrate) and SPR and of labelled NAzyme substrates, for instance a mixture of an hydrophilic polymer, such as polyethylene glycol molecules (PEG-molecules) and NAzyme substrates that are labelled by a particle, for instance the NAzyme substrates are labelled by that they are covalently connected to the sensing surface of the SPR sensor detection zone and at the same time to the nanoparticle, and b) determination of the surface plasmon resonance-shift (SPR-shift) resulting from the NAzyme's activity. The bigger the SPR-shift towards lower resonance wavelengths, the higher the NAzyme concentration. The nanoparticles are adapted for signal enforcement once the particle-labelled NAzyme substrate on the SPR sensor detection zone is recognized by the NAzyme through hybridization. Upon hybridization and recognition by the NAzyme, the particle is released by cleavage and dehybridization, which is monitored by the SPR detection zone since it is a mass-sensitive technique. Labelling of the NAzyme substrates (sensitive to NAzyme cleavage activity) with particles is essential, as the released substrate parts without particles are too low in mass to generate a reliable SPR signal. After dehybridization the NAzyme can bind a next NAzyme substrate in case of multiple-turnover conditions. In a further specific embodiments, the particles have diameters ranging from about 3 nanometer to about 300 nanometers. The NAzyme can be for instance DNAzyme, or activity of NAzymes combined with substrate of another NAzyme, for instance MNAzyme combined by a target substrate of another MNAzyme. Each possibility represents a separate embodiment of the present invention.

In another aspect of the invention, the NAzyme activity in a fluid is measured by a surface plasmon resonance (SPR) biosensor. The technique includes: a) incubation of the fluid comprising an unknown NAzyme concentration with the SPR sensor detection zone of which the sensing surface is covered or surface coated with a mixture of substance that prevents or minimize nonspecific interaction between analyte (physical adsorption of the substrate) and SPR and of labelled NAzyme substrates, for instance a mixture of an hydrophilic polymer, such as polyethylene glycol molecules (PEG-molecules) and NAzyme substrates that are labelled by a metallic particle, for instance the NAzyme substrates are labelled by that they are covalently connected to the sensing surface of the SPR sensor detection zone and at the same time to the metallic particle (for instance to gold nanoparticles (AuNPs), and b) determination of the surface plasmon resonance-shift (SPR-shift) resulting from the NAzyme's activity. The bigger the SPR-shift towards lower resonance wavelengths, the higher the NAzyme concentration. The metallic particles are adapted for signal enforcement once the metallic particle-labelled NAzyme substrate on the SPR sensor detection zone is recognized by the NAzyme through hybridization. Upon hybridization and recognition by the NAzyme, the metallic particle is released by cleavage and dehybridization, which is monitored by the SPR detection zone since it is a mass-sensitive technique. Labelling of the NAzyme substrates (sensitive to NAzyme cleavage activity) with metallic particles is essential, as the released substrate parts without metallic particles are too low in mass to generate a reliable SPR signal. After dehybridization the NAzyme can bind a next NAzyme substrate in case of multiple-turnover conditions. Such metallic particles comprise a metal, preferably an inert metal and furthermore they may have a selected morphology for instance a morphology selected from a cubic, a spherical, polyhedron and a spheroidal morphology or the shape can be asymmetric, for instance in the shape of nanorod. Metallic particles can be monometallic or bimetallic (e.g. Au—Ag, Pd—Ag, Pt—Ag and Pd—Au) dimers. In a further specific embodiments, the metallic particles have diameters ranging from about 3 nanometer to about 300 nanometers. The NAzyme can be for instance DNAzyme, or activity of NAzymes combined with substrate of another NAzyme, for instance MNAzyme combined by a target substrate of another MNAzyme. Each possibility represents a separate embodiment of the present invention.

In more particular aspect of the invention, the NAzyme activity in a fluid is measured by a fiber optic surface plasmon resonance (FO-SPR) biosensor. The technique includes: a) incubation of the fluid comprising an unknown NAzyme concentration with a FO-SPR sensor of which the sensing surface is covered or surface coated with a mixture of substance that prevents or minimize nonspecific interaction between analyte (physical adsorption of the substrate) and FO-SPR sensor surface with labelled NAzyme substrates, for instance a mixture of an hydrophilic polymer, such as polyethylene glycol molecules (PEG-molecules) and NAzyme substrates that are labelled by a metallic particle, for instance the NAzyme substrates are labelled by that they are covalently connected to the sensing surface [2] of the FO-SPR sensor [1] and at the same time to the metallic particle (for instance to AuNP with gold nanoparticles (AuNPs), and b) determination of the surface plasmon resonance-shift (SPR-shift) resulting from the NAzyme's activity. The bigger the SPR-shift towards lower resonance wavelengths, the higher the NAzyme concentration. The metallic particles are adapted for signal enforcement once the metallic particle-labelled NAzyme substrate on the FO-SPR sensor surface is recognized by the NAzyme through hybridization. Upon hybridization and recognition by the NAzyme, the metallic particle is released by cleavage and dehybridization, which is monitored by the FO-SPR since it is a mass-sensitive technique. In particular when crude sample matrices are analyzed, labelling of the NAzyme substrates (sensitive to NAzyme cleavage activity) with metallic particles, prevents that the released substrate parts without metallic particles are too low in mass to generate a reliable FO-SPR signal, and prevents non-specific signal generation. After dehybridization the NAzyme can bind a next NAzyme substrate in case of multiple-turnover conditions. Such metallic particles comprise a metal, preferably an inert metal and furthermore they may have a selected morphology for instance a morphology selected from a cubic, a spherical, polyhedron and a spheroidal morphology or the shape can be asymmetric, for instance in the shape of nanorod. Metallic particles can be monometallic or bimetallic (e.g. Au—Ag, Pd—Ag, Pt—Ag and Pd—Au) dimers. In a further specific embodiments, the metallic particles have diameters ranging from about 3 nanometer to about 300 nanometers. The NAzyme can be for instance DNAzyme, or activity of NAzymes combined with substrate of another NAzyme, for instance MNAzyme combined with substrate of another MNAzyme. Each possibility represents a separate embodiment of the present invention.

In particular aspect of the invention, the NAzyme activity in a fluid is measured by a surface plasmon resonance (SPR) biosensor. The technique includes: a) incubation of the fluid comprising an unknown NAzyme concentration with a SPR sensor detection zone of which the sensing surface is covered or surface coated with a mixture of substance that prevents or minimize nonspecific interaction between analyte (physical adsorption of the substrate) and SPR and of labelled NAzyme substrates, for instance a mixture of an hydrophilic polymer, such as polyethylene glycol molecules (PEG-molecules) and labelled NAzyme substrates, for instance NAzyme substrates labelled with gold nanoparticles (AuNPs), and b) determination of the surface plasmon resonance-shift (SPR-shift) resulting from the NAzyme's activity. The bigger the SPR-shift towards lower resonance wavelengths, the higher the NAzyme concentration.

In yet a more particular aspect of the invention, the NAzyme activity in a fluid is measured by a fiber optic surface plasmon resonance (FO-SPR) biosensor. The technique includes: a) incubation of the fluid comprising an unknown NAzyme concentration with a FO-SPR sensor of which the sensing surface is covered or surface coated with a mixture of substance that prevents or minimize nonspecific interaction between analyte (physical adsorption of the substrate) and FO-SPR and of labelled NAzyme substrates, for instance a mixture of an hydrophilic polymer, such as polyethylene glycol molecules (PEG-molecules) and labelled NAzyme substrates, for instance NAzyme substrates labelled with gold nanoparticles (AuNPs), and b) determination of the surface plasmon resonance-shift (SPR-shift) resulting from the NAzyme's activity. The bigger the SPR-shift towards lower resonance wavelengths, the higher the NAzyme concentration.

In yet one aspect of the invention, the DNAzyme activity in a fluid is measured by a surface plasmon resonance (SPR) biosensor. The technique includes: a) incubation of the fluid comprising an unknown DNAzyme concentration with a SPR sensor detection zone of which the sensing surface is covered with a mixture of PEG-molecules and DNAzyme substrates labelled with gold nanoparticles (AuNPs) and b) determination of the surfaced plasmon resonance-shift (SPR-shift) resulting from the DNAzyme's activity. The bigger the SPR-shift towards lower resonance wavelengths, the higher the DNAzyme concentration.

In yet a more particular aspect of the invention, the DNAzyme activity in a fluid is measured by a fiber optic surface plasmon resonance (FO-SPR) biosensor. The technique includes: a) incubation of the fluid comprising an unknown DNAzyme concentration with a FO-SPR sensor of which the sensing surface is covered with a mixture of PEG-molecules and DNAzyme substrates labelled with gold nanoparticles (AuNPs) and b) determination of the surfaced plasmon resonance-shift (SPR-shift) resulting from the DNAzyme's activity. The bigger the SPR-shift towards lower resonance wavelengths, the higher the DNAzyme concentration.

In another aspect of this disclosure, the invention provides a ligation method to manufacture the presented surface plasmon resonance (SPR) sensor including following components:
a) a SPR sensor surface comprising at least one first single DNA strand with distinct sequence, called SPR-probe, immobilized on the detection or sensing surface of said the SPR sensor,
b) a nanoparticle comprising a second single DNA strand with distinct sequence, hereinafter called nanoparticle-probe, immobilized on said the nanoparticle,
c) a third single DNA strand with distinct sequence, called ligation template, to align the SPR-probe and nanoparticle-probe by partial hybridization with the ligation template to form one hybridized complex and
d) a selected ligase to ligate together the SPR-probe and nanoparticle-probe to a specific single stranded DNA construct between the SPR sensor surface and a nanoparticle. The ligated DNA construct is designed to function as a specific nanoparticle-labelled NAzyme substrate. An advantageous technical effect of present invention is avoiding the presence of full substrates which are not linked between the surface and nanoparticle. Such nanoparticles can be electrically chargeable, for instance it is metallic or comprises a metal, preferably an inert metal and furthermore it may have a selected morphology for instance a morphology selected from a cubic, a spherical, polyhedron and a spheroidal morphology or the shape can be asymmetric, for instance in the shape of nanorod. Metallic nanoparticles can be monometallic or bimetallic (e.g. Au—Ag, Pd—Ag, Pt—Ag and Pd—Au) dimers. In a further specific embodiments, the nanoparticles have diameters ranging from about 3 nanometer to about 300 nanometers. The NAzyme can be for instance DNAzyme, or activity of NAzymes combined with substrate of another NAzyme, for instance DNAzyme combined with substrate of another DNAzyme. Each possibility represents a separate embodiment of the present invention.

In yet another more particular aspect of this disclosure, the invention provides a ligation method to manufacture the presented FO-SPR sensor [1] including following components:
a) a FO-SPR sensor surface [2] comprising at least one first single DNA strand with distinct sequence [4], called FO-SPR probe, immobilized on the sensing surface [2] of said the FO-SPR sensor [1],
b) a nanoparticle [9] comprising a second single DNA strand with distinct sequence [5], hereinafter called nanoparticle-probe, immobilized on said the nanoparticle,
c) a third single DNA strand with distinct sequence, called ligation template [6], to align the FO- and nanoparticle-probe by partial hybridization with the ligation template to form one hybridized complex of [4], [5] and [6] and
d) a selected ligase [8] to ligate together the FO-SPR and nanoparticle-probe to a specific single stranded DNA construct [7] between the FO-SPR sensor surface and a nanoparticle. The ligated DNA construct is designed to function as a specific nanoparticle-labelled NAzyme substrate. An advantageous technical effect of present invention is avoiding the presence of full substrates which are not linked between the surface and nanoparticle. The legend numbers between brackets [ ] refer to FIG. 1. Such nanoparticles can be electrically chargeable, for instance it is metallic or comprises a metal, preferably an inert metal and furthermore it may have a selected morphology for instance a morphology selected from a cubic, a spherical, polyhedron and a spheroidal morphology or the shape can be asymmetric, for instance in the shape of nanorod. Metallic nanoparticles can be monometallic or bimetallic (e.g. Au—Ag, Pd—Ag, Pt—Ag and Pd—Au) dimers. In a further specific embodiments, the nanoparticles have diameters ranging from about 3 nanometer to about 300 nanometers. The NAzyme can be for instance DNAzyme, or activity of NAzymes combined with substrate of another NAzyme, for instance DNAzyme combined with substrate of another DNAzyme or for instance MNAzyme combined with substrate of another MNAzyme. Each possibility represents a separate embodiment of the present invention.

In yet another specific aspect of this disclosure, the invention provides a ligation method to manufacture the presented SPR sensor detection zone of an SPR sensor including following components:
a) a SPR sensor surface comprising at least one first single DNA strand with distinct sequence, called SPR-probe, immobilized on the sensing surface of said the SPR sensor detection zone, b) gold nanoparticles (AuNPs) comprising a second single DNA strand with distinct sequence, hereinafter called AuNP-probe, immobilized on said the AuNPs, c) a third single DNA strand with distinct sequence, called ligation template, to align the SPR-probe and AuNP-probe by partial hybridization with the ligation template to form one hybridized complex and d) a selected ligase to ligate together the SPR- and AuNP-probe to a specific single stranded DNA construct between the SPR sensor surface and a AuNP. The ligated DNA construct is designed to function as a specific AuNP-labelled NAzyme substrate. An advantageous technical effect of present invention is avoiding the presence of full substrates which are not linked between the surface and AuNPs. Such gold nanoparticles can have a morphology selected from a cubic, a spherical, polyhedron and a spheroidal morphology or the shape can be asymmetric, for instance in the shape of nanorod. In a further specific embodiments, the gold nanoparticles have diameters ranging from about 3 nanometer to about 300 nanometers. The NAzyme can be for instance DNAzyme, or activity of NAzymes combined with substrate of another NAzyme, for instance DNAzyme combined with substrate of another DNAzyme. Each possibility represents a separate embodiment of the present invention.

In yet more particular specific aspect of this disclosure, the invention provides a ligation method to manufacture the presented FO-SPR sensor [1] including following components:

a) a FO-SPR sensor surface [2] comprising at least one first single DNA strand with distinct sequence [4], called FO-SPR probe, immobilized on the sensing surface [2] of said the FO-SPR sensor [1], b) gold nanoparticles (AuNPs) [9] comprising a second single DNA strand with distinct sequence [5], hereinafter called AuNP-probe, immobilized on said the AuNPs, c) a third single DNA strand with distinct sequence, called ligation template [6], to align the FO- and AuNP-probe by partial hybridization with the ligation template to form one hybridized complex of [4], [5] and [6] and d) a selected ligase [8] to ligate together the FO- and AuNP-probe to a specific single stranded DNA construct [7] between the FO-SPR sensor surface and a AuNP. The ligated DNA construct is designed to function as a specific AuNP-labelled NAzyme substrate. An advantageous technical effect of present invention is avoiding the presence of full substrates which are not linked between the surface and AuNPs. The legend numbers between brackets [ ] refer to FIG. 1.

Such gold nanoparticles can have a morphology selected from a cubic, a spherical, polyhedron and a spheroidal morphology or the shape can be asymmetric, for instance in the shape of nanorod. In a further specific embodiments, the gold nanoparticles have diameters ranging from about 3 nanometer to about 300 nanometers. The NAzyme can be for instance DNAzyme, or activity of NAzymes combined with substrate of another NAzyme, for instance DNAzyme combined with substrate of another DNAzyme. Each possibility represents a separate embodiment of the present invention.

In a particular embodiment, the device according to the present invention comprises this ligation method, whereby the FO-SPR sensor and nanoparticle surface, e.g. the AuNPs surfaces, are backfilled with PEG-molecules prior to ligation. Alternatively PEG-molecules are replaced by other substances that prevents or minimize nonspecific interaction between analyte (physical adsorption of the substrate), for instance hydrophilic polymers.

In another embodiment of the method to measure NAzyme (e.g. DNAzyme) activity, these NAzyme activity sensors are characterised in that the sensor comprises a FO-SPR sensor surface [1] adapted to measure NAzyme activity by NAzyme substrates that each are covalently connected to the sensing surface [2] of the FO-SPR sensor [1] and at the same time to a AuNP [9]. The AuNPs are adapted for signal enforcement once the AuNP-labelled NAzyme substrate on the FO-SPR sensor surface is recognized by the NAzyme through hybridization. Upon hybridization and recognition by the NAzyme, the AuNP is released by cleavage and dehybridization, which is monitored by the FO-SPR since it is a mass-sensitive technique. Labelling of the NAzyme substrates (sensitive to NAzyme cleavage activity) with AuNPs is essential, as the released substrate parts without AuNPs are too low in mass to generate a reliable FO-SPR signal. After dehybridization the NAzyme can bind a next NAzyme substrate in case of multiple-turnover conditions. Yet another embodiment is the use of the NAzyme-based bioassay on FO-SPR platform of present invention for (i) monitoring molecular binding events in real-time, (ii) detecting and quantifying a variety of molecules (proteins, DNA, small molecules) in biological samples and (iii) nanoparticle based signal amplification.

Yet another embodiment is the use of the NAzyme-based bioassay of present invention ligating a solid surface to a nanoparticle and using the FO-SPR platform for (i) monitoring molecular binding events in real-time, (ii) detecting and quantifying a variety of molecules (proteins, DNA, small molecules) in biological samples and (iii) nanoparticle based signal amplification and (iv) DNA sequence specific nanoparticle probe detection.

Some embodiments of the invention are set forth in claim format directly below:

1) A NAzyme activity surface plasmon resonance sensor, characterised in that the sensor comprises a DNA probe (4) covalently connect to a sensing surface (2) and a DNA probe (5) covalently connected to a nanoparticle or covalently connected to a nanoparticle cluster (9) whereby the DNA probe of the sensing surface (4) and the DNA probes (5) of the particle or particle cluster (9) are ligated together to a selected single strand DNA construct (7) comprising the ligation zone (18) within a selected NAzyme substrate (12) so that said sensor is adapted to measure DNAzyme activity by NAzyme binding at the NAzyme substrate (12) and cleavage at the ligation zone (18).

2) A fiber optic surface plasmon resonance sensor tip (1) for measuring NAzyme activity or for measuring cleaving activity of enzyme on DNA substrate, characterised in that a single strand DNA (7) with a NAzyme substrate and a ligation zone (18) is covalently connected to said the sensing surface (2) of the fiber optic surface plasmon resonance sensor tip (1) and at the same time is covalently connected to a metallic nanoparticle so that sensor is adapted to measure a selected NAzyme activity when the NAzyme substrate (12) is recognized by the NAzyme through hybridization and the metallic nanoparticle is released by cleavage of said the single strand DNA (7) that covalently binds to the sensing surface (2) and to the metallic particle or the metallic particle cluster (9).

3) The sensor according to any one of the embodiments 1 to 2, whereby the ligated single strand DNA probe (7) that covalently binds to the sensing surface (2) and to the nanoparticle (9) comprises the ligation zone (18) within the NAzyme substrate (12) for the selected NAzyme (17).
4) A sensor kit with the sensor according to any one of the embodiments 1 to 3, further comprising a reversible NAzyme inhibitor.
5) A sensor kit with the sensor according to any one of the embodiments 1 to 4, further comprising an inhibitor strand or a NAzyme blocking DNA sequence, said inhibitor comprising a NAzyme binding arm and an internal loop for binding of a specific target independent of the catalytic activity from NAzyme binding arms.
6) A sensor kit with the sensor according to any one of the embodiments 1 to 5, whereby the target is of the group consisting of a peptide, a polypeptides, a sugar, a protein, a small molecules, a nucleotide and a fat group.
7) A sensor kit with the sensor according to any one of the embodiments 1 to 6, whereby the NAzyme inhibitor comprises a NAzyme blocking DNA sequence and a target recognition aptamer.
8) A sensor kit with the sensor according to any one of the embodiments 1 to 7, whereby the metallic nanoparticle is gold nanoparticle (AuNP).
9) The sensor or sensor kit according to any one of the embodiments 11 to 8, whereby the sensing surface (2) is covered by a gold coating.
10) The sensor or sensor kit according to any one of the embodiments 1 to 9, comprising a selected NAzyme-substrate SPR-metallic nanoparticle-probe.
11) The use of the sensor or sensor kit according to any one of the embodiments 1 to 10, for real-time monitoring system of NAzyme cleavage activity in function of binding of selected targets.
12) The use of the sensor or sensor kit according to any one of the embodiments 1 to 10, for temporary inactivating a target NAzyme in the absence of a selected target and activating the NAzyme activity in function of the presence of the selected target.
13) The use of the sensor or sensor kit according to any one of the embodiments 1 to 10, for monitoring molecular binding events in real-time.
14) The use of the sensor or sensor kit according to any one of the embodiments 1 to 10, for detecting and quantifying a variety of molecules (proteins, DNA, small molecules) in biological samples.
15) The use of the sensor or sensor kit according to any one of the embodiments 1 to 10, for nanoparticle based signal amplification.
16) The use of the sensor or sensor kit according to any one of the embodiments 1 to 10, in analysis method with the steps 1) activated NAzyme cleaves Nazyme substrate complex which is eventually after an inhibited NAzyme is activated or a NAzyme is amplified by target, 2) FO-SPR hybridization and 3) melt analysis combined with NAzyme amplification.
17) A method of functionalizing the sensing surface (2) of a surface plasmon resonance (SPR) sensor (1) for sensing nucleic acid enzyme (NAzyme) activity in a fluid or for or measuring enzyme activity on a selected DNA substrates, the method comprising,
providing the sensing surface (2) comprising at least one first single strand DNA with distinct sequence (4) immobilized on the sensing surface (2) of said the sensor (1)
providing a nanoparticle or nanoparticle cluster (9) comprising a second single strand DNA with distinct sequence (5) immobilized on said the nanoparticle or the nanoparticle cluster
providing a third distinct DNA sequence being ligation template (6) for said first single strand (4) and second single strand (5) for DNA hybridizing the third distinct DNA sequence ligation template (6) in part with said the first single strand DNA and in part with the second single strand DNA to form a SPR probe and nanoparticle-probe complex or a SPR probe and nanoparticle cluster-probe complex
providing a selected ligase to ligate together to a selected single strand DNA construct (7) that incorporates a NAzyme substrate (12) for the selected NAzyme (17) between nanoparticle and SPR sensing surface (2) or between the nanoparticle cluster (9) and SPR sensing surface (2).
18) A method of manufacturing a fiber optic surface plasmon resonance sensor tip (1) for sensing NAzyme activity in a fluid, the method comprising,
providing a fiber optic surface plasmon resonance sensor (FO-SPR) tip (1) comprising at least one first single strand DNA with distinct sequence (4) immobilized on the sensing surface (2) of said the fiber optic surface plasmon resonance sensor tip (1)
providing metallic nanoparticles (9) comprising a second single strand DNA with distinct sequence (5) immobilized on said the metallic nanoparticles (9)
providing a third distinct DNA sequence being a ligation template (6) for said first single strand (4) and second single strand (5) for DNA hybridizing the third distinct DNA sequence ligation template (6) in part with said the first single strand DNA and in part with the second single strand DNA to form one FO-SPR probe and metallic nanoparticle-probe complex
providing a selected ligase (8) to ligate together to a selected single strand DNA construct (7) that incorporates a NAzyme substrate (12) for the selected NAzyme (17) between metallic nanoparticle and FO-SPR sensor tip (1).
19) The method according to any one of the embodiments 17 to 18, whereby the sequence of the NAzyme (17) hybridizing to the single strand DNA structure (7) coincides with the ligation zone (18) to only obtain available substrate for the NAzyme (17) when the FO-SPR sensor is linked through a single strand with a nanoparticle.
20) The method according to any one of the embodiments 17 to 19, whereby the sensing surface (2) and metallic nanoparticle surfaces are coated with substance that prevents or minimize nonspecific interaction of analyte prior to ligation.
21) The method according to any one of the embodiments 17 to 19, whereby the sensing surface (2) and metallic nanoparticle surfaces are coated with an hydrophilic polymer prior to ligation.
22) The method according to any one of the embodiments 17 to 19, whereby the sensing surface (2) and metallic nanoparticle surfaces are coated with polyethylene glycol molecules (3) (PEG-molecules) prior to ligation.
23) The method according to any one of the embodiments 17 to 22, where by the metallic nanoparticle is a gold nanoparticle (AuNP).

24) The method according to any one of the embodiments 17 to 23, where by the sensing surface (2) to be functionalized has an upper gold (Au) surface.

25) The method according to any one of the embodiments 17 to 24, where by the NAzymes (17) to be analysed is selected of the group consisting of a DNAzyme, a NAzymes combined with substrate of another NAzyme and a DNAzyme combined with substrate of another DNAzyme.

26) A method of analysing an active NAzyme or NAzyme activity in a fluid or of analysing in said enzyme on DNA substrate, the method comprising exposing the functionalized sensing surface (2) manufactured according to any one of the methods 17 to 25, to a fluid to be analysed for NAzyme activity.

27) A method of analysing an active NAzyme or NAzyme activity in a fluid or of analysing in said enzyme on DNA substrate, the method comprising exposing the functionalized fiber optic surface plasmon resonance sensor tip (1) manufactured according to any one of the methods 17 to 25, to a fluid to be analysed for NAzyme activity.

28) The method according to any one of the embodiments 26 or 27, characterised in that it is adapted for signal enforcement by that when NAzyme substrate (12) on DNA probe (7) connecting the sensing surface (2) and the metallic nanoparticle or metallic nanoparticle cluster (9) is recognized by the NAzyme through hybridization the metallic nanoparticle or metallic nanoparticle cluster (9) is released by cleavage so that after cleavage the NAzyme binds a next NAzyme substrate of another DNA probe (7) connecting the sensing surface (2) and a metallic nanoparticle or metallic nanoparticle cluster (9).

Some other embodiments of the invention are set forth in claim format directly below:

1) A NAzyme activity sensor system, characterised in that the sensor system comprises a NAzyme substrate complex (25) that comprises a first DNA probe (4) covalently connected to microcarrier (19) and a second DNA probe (5) covalently connected to a nanoparticle or nanoparticle cluster (9) whereby the DNA probe of the microcarrier (19) and the DNA probes (5) of the nanoparticle or nanoparticle cluster (9) are ligated together to a selected single strand DNA construct (7) comprising the ligation zone (18) and a selected NAzyme substrate (12) and whereby the sensing system further comprises a to the second DNA probe (5) complementary single strand DNA probe (22) covalently bound to the sensing surface (2) of a sensor (1) so that said sensor is adapted to measure DNAzyme activity by NAzyme binding at the NAzyme substrate (12) and cleavage at the ligation zone (18).

2) The sensing system according to embodiment 1, further comprising a another comprises a NAzyme substrate complex (25) with a different selected NAzyme substrate (12), whereof a complementary single strand DNA probe (22) covalently bound to the sensing surface (2) of a sensor (1) so that said sensor is adapted to multiplex measure DNAzyme activity.

3) The sensing system according to any one of the embodiments 1 to 2, characterised in that the sensing surface (2) is of a surface plasmon resonance sensor (1).

4) The sensing system according to embodiment 1, characterised in that the sensing surface (2) is of a fiber optic surface plasmon resonance sensor (FO-SPR) tip (1).

5) The sensing system according to any one of the embodiments 1 to 3, whereby the ligated single strand DNA probe (7) that covalently binds to the sensing surface (2) and to the nanoparticle (9) comprises the ligation zone (18) within the NAzyme substrate (12) for the selected NAzyme (17).

6) The sensing system according to any one of the embodiments 1 to 4, further comprising a reversible NAzyme inhibitor.

7) The sensing system according to any one of the embodiments 1 to 5, further comprising an inhibitor strand or a NAzyme blocking DNA sequence, said inhibitor comprising a NAzyme binding arm and an internal loop for binding of a specific target independent of the catalytic activity from NAzyme binding arms.

8) The sensing system according to any one of the embodiments 1 to 6, whereby the target is of the group consisting of a peptide, a polypeptides, a sugar, a protein, a small molecules, a nucleotide and a fat group.

9) The sensing system to any one of the embodiments 1 to 7, whereby the NAzyme inhibitor comprises a NAzyme blocking DNA sequence or a target recognition aptamer.

10) The sensing system according to any one of the embodiments 1 to 7, whereby the nanoparticle is metallic particle 11) The sensing system according to any one of the embodiments 1 to 7, whereby the nanoparticle is a gold nanoparticle (AuNP).

12) The sensing system according to any one of the embodiments 1 to 11, whereby the sensing surface (2) is covered by a gold coating.

13) Use of the sensing system according to any one of the embodiments 1 to 112, for real-time monitoring system of NAzyme cleavage activity in function of binding of selected targets.

14) Use of the sensing system according to any one of the embodiments 1 to 12, for temporary inactivating a target NAzyme in the absence of a selected target and activating the NAzyme activity in function of the presence of the selected target.

15) Use of the sensing system according to any one of the embodiments 1 to 12, for monitoring molecular binding events in real-time.

16) Use of the sensing system according to according to any one of the embodiments 1 to 12, for detecting and quantifying a variety of molecules (proteins, DNA, small molecules) in biological samples.

17) Use of the sensing system according to t according to any one of the embodiments 1 to 12, for nanoparticle based signal amplification.

18) Use of the sensing system according to any one of the embodiments 1 to 12, in analysis method with the steps 1) activated NAzyme cleaves Nazyme substrate complex which is eventually after an inhibited NAzyme is activated or a NAzyme is amplified by target, 2) FO-SPR hybridization and 3) melt analysis combined with NAzyme amplification.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

DETAILED DESCRIPTION OF EMBODIMENTS OF THE INVENTION

Definitions

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only.

Each and every claim is incorporated into the specification as an embodiment of the present invention. Thus, the claims are part of the description and are a further description and are in addition to the preferred embodiments of the present invention.

Each of the claims set out a particular embodiment of the invention.

The following terms are provided solely to aid in the understanding of the invention.

By the terms "microcarrier" as used herein is meant any solid particle of 1000 microns or less in diameter or length, of virtually any shape, for instance also a rod. The carriers according to the invention have a diameter of length of 1000 microns (corresponding to 18 mesh according to the US Bureau of Standards) or less, on average, preferably of 600 microns (30 mesh) or less, in particular of 250 microns (60 mesh) or less, for example about 40 microns (400 mesh). The carriers can also be smaller. For instance, carriers having, on average, a diameter of length of 0.05 to 40, in particular 1 to 20 or 1 to 10 microns can be used. A particularly preferred embodiment of the carriers according to the instant invention has, on average, a diameter of length of 1 to 250 microns, in particular 3 to 180 microns. The average particle diameter of lengths can, for instance, be determined by sieving techniques or, particularly in case of diameter of lengths below of 40 microns, by scanning electron microscopy.

In the instant application the term "microbead" means solid particles which are substantially regularly curved and which are substantially free of sharp edges. Preferably the microbeads have a substantially spherical shape. The microbeads according to the invention have a diameter of 1000 microns (corresponding to 18 mesh according to the US Bureau of Standards) or less, on average, preferably of 600 microns (30 mesh) or less, in particular of 250 microns (60 mesh) or less, for example about 40 microns (400 mesh). The microbeads can also be smaller. For instance, microbeads having, on average, a diameter of 0.05 to 40, in particular 1 to 20 or 1 to 10 microns can be used. A particularly preferred embodiment of the microbeads according to the instant invention has, on average, a diameter of 1 to 250 microns, in particular 3 to 180 microns. The average particle diameters can, for instance, be determined by sieving techniques or, particularly in case of diameters below of 40 microns, by scanning electron microscopy.

"Nucleic acid enzymes" (NAzymes) refers to nucleic acid sequences with activities similar to enzymes, thereby being able to modify, cleave or ligate their target upon recognition. These nucleic acid sequences include: DNA or DNA-containing molecules (known as deoxyribozymes or DNAzymes) which catalyse their substrate as mentioned above upon recognition and DNA or DNA-containing molecules designed as inactive subunits of nucleic acid enzymes, only showing activity if all subunits are combined (known as multi-component nucleic acid enzymes or MNAzymes or binary deoxyribozymes). NAzymes are oligonucleotides with enzymatic capabilities, including RNA and RNA-DNA hybrid cleavage, peroxidase activity [13], Friedel-Crafts reaction [14], and porphyrin metalation [15]. RNA/RNA-DNA hybrid cleaving NAzyme comprises of a catalytic core flanked by two substrate binding arms involved in hybridization with the specific substrate by virtue of Watson-Crick base pairing both present on the uncleaved substrate.

DNAzyme and multi-component nucleic acid enzyme (MNAzymes) are nucleic acid-based enzymes (NAzymes), which infiltrated the otherwise protein-rich field of enzymology three decades ago. The 10-23 core NAzymes are one of the most widely used and well-characterized NAzymes, but often require elevated working temperatures or additional complex modifications for implementation at standard room temperatures. Such 10-23 DNAzyme contains a 15-nucleotide catalytic core that is flanked by two substrate recognition domains.

MNAzymes are derived from their parent DNAzymes via division of the catalytic core into two halves, and addition of two binding arms to each of the partial catalytic cores. Thus, the MNAzymes assemble in their catalytic form only in the presence of a facilitator oligonucleotide, binding with the target-binding arms of the MNAzyme and enabling cleavage of substrate, binding to the other two arms [16]. MNAzymes only form catalytic core in the presence of an assembly facilitator.

"MNAzyme" as used herein have the same meaning and refer to two or more oligonucleotide sequences which, only in the presence of an MNAzyme assembly facilitator (for example, a target), form an active nucleic acid enzyme that is capable of catalytically modifying a substrate. MNAzymes can catalyse a range of reactions including cleavage of a substrate, ligation of substrates and other enzymatic modifications of a substrate or substrates. MNAzyme comprise bipartite structures, composed of two molecules, or tripartite structures, composed of three nucleic acid molecules, or other multipartite structures, for example those formed by four or more nucleic acid molecules. MNAzyme as used herein encompass all known MNAzymes and modified MNAzymes including those disclosed in any one or more of PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety). Non-limiting examples of MNAzymes and modified MNAzymes encompassed by the terms "MNAzyme" and include MNAzymes with cleavage catalytic activity (as exemplified herein), disassembled or partially assembled MNAzymes comprising one or more assembly inhibitors, MNAzymes comprising one or more aptamers ("apta-MNAzymes"), MNAzymes comprising one or more truncated sensor arms and optionally one or more stabilizing oligonucleotides, MNAzymes comprising one or more activity inhibitors, multi-component nucleic acid inactive proenzymes (MNAi), and MNAzymes with ligase catalytic activity ("MNAzyme ligases"), each of which is described in detail in one or more of WO/2007/041774, WO/2008/040095, WO2008/122084, US 2007-0231810, US 2010-0136536, and/or US 2011-0143338.

"FO-SPR sensor" refers to the entire optical fiber embedded in a connector as described previously (Arghir et al. and Lu et al.).

"AuNP or AuNPs" is used to refer to gold nanoparticle(s).

"FO-SPR and AuNP-probe(s)" is used to distinguish the ssDNA sequences that were immobilized on the gold surface of the FO-SPR sensor and the surface of the AuNPs respectively.

"Ligation Template" refers to the ssDNA sequence used to align the FO-SPR and AuNP-probe and create the nick to be ligated by the ligase.

"DNAzyme substrate" in this patent refers to the complete sequence immobilized between the gold surface of the FO-SPR sensor and AuNPs. Therefore, every DNAzyme substrate as defined here must be ligated.

A nanoparticles can be formed of a variety of materials. Non-limiting examples of suitable nanoparticle materials include glass, polystyrene, noble metals such as gold, silver, platinum, iridium, palladium, rhodium, ruthenium and osmium, semiconductors such as CdS, CdSe, ZrO2 and TiO2, alloys thereof, intermetallics thereof, and combinations thereof. In one specific aspect, the nanoparticles are comprised of gold. In another aspect of the invention the nanoparticle is a protein, DNA, RNA based nanostructure, in case of a DNA nanostructure for instance a tetrahedral DNA. In one aspect, the nanoparticles can be homogeneous, single phase particles which consist essentially of a single material. In this document, the term nanoparticle shall be understood to mean particles having at least one dimension equal to or less than 500 nm, preferably equal to or less than 300 nm, more preferably equal to or less than 100 nm in a particular aspect the nanoparticles are on the minute end of the nanoparticle size range, although larger nanoparticles may also be suitable for some applications. In one aspect, the nanoparticle has an average particle diameter from about 1 nm to about 30.

Nanoparticles can be electrically chargeable, for instance it is metallic or comprises a metal, preferably an inert metal and furthermore it may have a selected morphology for instance a morphology selected from a cubic, a spherical, polyhedron and a spheroidal morphology or the shape can be asymmetric, for instance in the shape of nanorod. Metallic nanoparticles can be monometallic or bimetallic (e.g. Au—Ag, Pd—Ag, Pt—Ag and Pd—Au) dimers. In a further specific embodiments, the nanoparticles have diameters ranging from about 3 nanometer to about 300 nanometers. The NAzyme can be for instance DNAzyme, or activity of NAzymes combined with substrate of another NAzyme, for instance DNAzyme combined with substrate of another DNAzyme. Each possibility represents a separate embodiment of the present invention. Metallic nanoparticles display intense colours due to absorption and scattering and localized surface plasmon resonance. Nanoparticle size differences and clusters lead to changes in colour and these colours can be altered by changes in size or aggregation of the nanoparticles.

Nanoparticles can form clusters (the so-called "plasmonic molecules" or plasmonic nanoparticle clusters) and interact with each other to form cluster states. The symmetry of the nanoparticles and the distribution of the electrons within them can affect a type of bonding or antibonding character between the nanoparticles similarly to molecular orbitals. Since light couples with the electrons, polarized light can be used to control the distribution of the electrons and alter the mulliken term symbol for the irreducible representation. Changing the geometry of the nanoparticles can be used to manipulate the optical activity and properties of the system, but so can the polarized light by lowering the symmetry of the conductive electrons inside the particles and changing the dipole moment of the cluster. These clusters can be used to manipulate light on the nano scale. Metal nanoclusters are composed of a small number of atoms, at most in the tens. These nanoclusters can be composed either of a single or of multiple elements. Nanoclusters are smaller nanoparticles whose properties resemble those of molecules and thus are said to bridge the gap between the nanoparticle and the atom. Such nanoclusters exhibit attractive electronic, optical, and chemical properties compared to their larger counterparts.

Methods of in vitro nucleic acid amplification have widespread applications in genetics and disease diagnosis. Such methods include polymerase chain reaction (PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). Each of these target amplification strategies requires the use of oligonucleotide primers. The process of amplification results in the exponential amplification of amplicons which incorporate the oligonucleotide primers at their 5' termini and which contain newly synthesized copies of the sequences located between the primers. PASS oligonucleotides of the present invention may be used as primers (PASS primers) to amplify target nucleic acid sequences and to incorporate unique sequences (US) into resulting amplicons. No particular limitation exists in relation to amplification techniques to which the PASS primers may be applied. Amplicons generated by various reactions utilising the PASS oligonucleotides may be detected using any known technique. Non-limiting examples include those detection techniques using a signal provided by a dye that binds to double-stranded DNA (e.g. SYBR green), and/or those using an amplicon sequence specific-probe (e.g. molecular beacons, minor groove binder (MGB) probes, TaqMan® probes). In general, nucleic acid amplification techniques utilise enzymes (e.g. polymerases) to generate copies of a target nucleic acid that is bound specifically by one or more oligonucleotide primers. Non-limiting examples of amplification techniques in which PASS oligonucleotides may be used include one or more of the polymerase chain reaction (PCR), the reverse transcription polymerase chain reaction (RT-PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA). PASS primers contain a US composed of an antisense DNAzyme. Such PASS primers can be designed such that the unique sequence is composed of an inactive, antisense form of a DNAzyme while still being non-complementary to the target sequence. Upon amplification during PCR a catalytically active, sense DNAzyme can be inserted into the amplicon and can consequently cleave a substrate to produce a signal in real-time. PASS primers can be combined with MNAzyme qPCR such that MNAzymes comprise a first partzyme that binds to the complement of the unique sequence (cUS) as well as amplified target sequence. The second partzyme can bind adjacently to the first partzyme on the amplicon of interest. The active MNAzyme would then cleave a substrate 1 (Sub 1) to produce a signal that can be monitored in real-time. A second substrate 2 (Sub 2) can be added to both reactions, but when a standard PASS partzyme is used the substrate 2 would remain uncleaved and not produce a signal. However when the PASS primers are used that contain the antisense of the DNAzyme as the US, amplification results in formation of active DNAzymes that would cleave substrate 2 producing a signal that can be monitored in real-time. A positive control "standard" forward primers (non-PASS primers i.e. do not contain a US) can hereby be used to produce amplicons for the real-time detection and quantification of a specific nucleotide target DNA (specific for the forward primer and a universal reverse primer) by MNAzymes binding only to the target sequence of interest (17). This method allows amplification a target with DNAzyme.

An SPR platform and in particular the FO-SPR platform has technical advantages: (i) it has the capability to monitor molecular binding events, which is considered an asset during the development of the assay, (ii) it has the unique capacity to quantify a variety of different molecules ranging from proteins and nucleic acids (NA)s to small molecules, meaning that newly developed assays in this project can be directly benchmarked to the existing ones on the FO-SPR irrespective of the selected target, (iii) it allows fast analysis and (iv) is userfriendly. The DNAzyme-based SPR biosensors has improved sensitivity, specificity and reproducibility.

In examples we describe the development of a real-time, in situ and sensitive biosensing concept using (i) DNAzymes for signal generation and amplification, (ii) modified gold nanoparticles ligated with the DNAzyme substrate to the biosensing surface to enhance the generated signal and (iii) FO-SPR as real-time readout system to create a universal assay concept, which needs minimal optimization for the detection of different biomarkers and can exceed the specificity and sensitivity of the individual component. The catalytic activity of DNAzymes forms the basis of the developed concept as it is responsible for generating the response signal. Therefore, the ligated substrates on the FO-SPR biosensor will be used to detect and characterize DNAzyme activity. On the one hand will this patent lead, in the future, to a universal DNAzyme-based biosensor for the detection of different biomarkers. On the other hand the described principle can be transferred for a broad range of new targets and nucleic acid enzymes without the labor-intensive assay development necessary for most standard techniques. Moreover, using only DNA molecules as assay components guarantees high robustness of the assay, while simplified readout and automation of the assay is being achieved with the use of a FO-SPR technology platform that has promising prospects in evolving towards a point-of-care device. Experiments have successfully demonstrated the functionalization of the FO-SPR sensor with AuNP-labelled DNAzyme substrates. Moreover, the SPR-shifts associated with ligation were controlled by changing the ligation temperature and concentration of the ligation template. It was shown that upon recognition and cleavage of the substrate, the DNAzyme caused release of the AuNPs, which was monitored continuously by the prefunctionalized FO-SPR sensor. In conclusion, a ligation-based, prefunctionalized FO-SPR sensor useful for the detection of DNAzyme activity was developed.

EXAMPLES

Example I Materials

All buffers were prepared with deionized water and reagents were purchased from The Merck group—Sigma-Aldrich (Bornem, Belgium), unless stated otherwise. Phosphate buffers were prepared with potassium dihydrogen phosphate from The Thermo Fisher Scientific group—Fisher Scientific (Merelbeke, Belgium) and dipotassium hydrogen phosphate from AppliChem GmbH (Darmstadt, Germany): 180 mM phosphate buffer (PB) at pH 8.0, 10 mM phosphate buffer with 0.01% (w/v) sodium dodecyl sulfate (PB-SDS) at pH 8.0 with and without 4 M NaCl purchased from The Thermo Fisher Scientific group—Fisher Scientific (Merelbeke, Belgium). Phosphate buffered saline (PBS) 10 mM at pH 7.4 was adapted up to 270 and 300 mM NaCl; together with 2-(N-morpholino)ethanesulfonic acid (MES) buffer 50 mM at pH 6.0, PBS was used in functionalization of the FO-SPR sensor. Tris buffers were prepared using Trizma® base: 10 mM Tris buffer with 1 mM Ethylenediaminetetraacetic acid (EDTA) purchased from Acros Organics (Geel, Belgium) at pH 8.0, 20 mM Tris buffer with and without 0.01% (w/v) SDS at pH 8.3 and 250 mM Tris at pH 9.4. Sodium hydroxide buffers were prepared with 2 M NaOH purchased from Chemlab (Zedelgem, Belgium): 50 mM NaOH buffer with 1 M NaCl. Dithiothreitol (DTT) was purchased from AppliChem GmbH, ethanol absolute from VWR Chemicals (Haasrode, Belgium) and Magnesium Chloride ($MgCl_2$) from The Merck group—Sigma-Aldrich (Bornem, Belgium). Both illustra NAP-5 columns and Immobiline DryStrip Cover Fluid were purchased from GE Healthcare Life Sciences (Diegem, Belgium) and streptavidin was purchased from The Thermo Fisher Scientific group—Fisher Scientific (Merelbeke, Belgium). Biotin-SAM formation reagent was produced by Dojindo Laboratories (Kumamoto, Japan) and AuNPs EMGC20 with a diameter of 20 nm by BBI Solutions (Cardiff, UK). The PEG MUA molecule ($C_{27}H_{55}NO_9S$), used as a backfilling molecule, was provided by Polypure AS (Oslo, Norway) and the Ampligase® Thermostable DNA Ligase with accompanying reaction buffer was provided by Epicentre® (Madison, USA). All DNA/RNA sequences were synthesized by Integrated DNA Technologies (IDT, Leuven, Belgium).

Sensor preparation and reaction buffers were the following: PB buffer (180 mM phosphate, pH 8), PB-SDS buffer (10 mM phosphate, 0.01% (w/v) SDS, pH 8.0), TE buffer (10 mM Tris, 1 mM EDTA, pH 8), Tris-SDS buffer (20 mM Tris buffer, 0.01% (w/v) SDS, pH 8.3) and DNAzyme reaction buffer (20 mM MgCl2, 50 mM Tris, 150 mM NaCl, pH 9.4).

Example II Methods

System Setup and Fabrication of the FO-Sensors

Real-time surface plasmon resonance (SPR) measurements were performed using the same fiber optic SPR (FO-SPR) platform as described by Arghir et al. and Lu et al. Briefly, the FO-SPR sensors were coupled to a bifurcated optical fiber with at one end a halogen light input and at the other end a spectrometer for the signal read-out. This complete system was mounted onto a robot setup to allow fully automated control of the FO-SPR sensors. The FO-SPR sensors were prepared from a multimode optical fiber (400 µm diameter) and have a final length of 4.3 cm with a sensing part of 0.6 cm from which the jacket and cladding were removed. Finally, the FO-SPR sensors were coated with a 50 nm gold layer prior to functionalization.

Example III AuNP Functionalization

Gold nanoparticle (AuNP) functionalization with single stranded DNA (ssDNA) using thiol chemistry was based on the method described by Hurst et al. and Knez et al. The DNA sequences to be put on the AuNPs or AuNP-probes (Table 1) were mixed with DTT to reduce the thiol-modified sequences before use. DTT (0.1 M dissolved in 0.18 M PB) was mixed with AuNP-probes to a final concentration of 50 mM and 50 µM respectively for 1 h at room temperature (RT). DTT will activate the thiol-dimers and was removed afterwards by purifying the activated AuNP-probes with illustra NAP-5 columns in TE buffer. AuNPs were upconcentrated by centrifugation for 20 min at 16,200 g and 20° C., removal of the supernatant and dissolving them in PB-SDS to a concentration of 3.87 nM. Directly after activation of the AuNP-probes, they were mixed with the upconcentrated AuNPs to a final concentration of 2.08 µM. Next, the AuNP solution was sonicated for 30 s and incubated for 20 min on a rotator at RT. A fast salt maturation protocol with 4 M NaCl in PB-SDS was used to maximize the DNA loading. After every salt addition the AuNP solution was again sonicated for 30 s and incubated for 20 min at RT. Once the final salt concentration was reached, the AuNP solution was further incubated overnight at RT. Next, the AuNPs were washed 3 times as following: centrifuging for 15 min at 16,200 g and 20° C., removing of the supernatant and dissolving in PB-SDS. After the third wash, the AuNPs were backfilled with PEG-molecules (5 mM dissolved in ethanol) by adding them to the AuNP-solution in a final concentration of 50 µM. After 1 h incubation at 4° C., the AuNPs were washed again as mentioned before, but after the third removal of the supernatant the AuNPs were dissolved in 200 µl DNAse-free water. Finally, the AuNP-solution was further diluted with DNAse-free water to an optical density (OD) of 2 in 150 µl at 530 nm using a 96-well plate and spectrophotometer. The beads were than stored at 4° C. until further use.

FO-SPR Sensor Surface Functionalization

Surface functionalization of the FO-SPR sensor was established using two different immobilization strategies: i) thiol chemistry and ii) streptavidin-biotin interaction. The first strategy is quite similar to the immobilization of the AuNP-probes described earlier. FO-SPR probes (Table 1) were activated with DTT and purified as described before to reduce the thiol-modified sequences. Once activated, the FO-SPR probes were mixed with 4 M NaCl in PB-SDS and diluted with PB-SDS to a final concentration of 1 µM FO-SPR probes and 1 M NaCl. Next, the sensitive part of four FO-SPR sensors were immersed in 150 µl of this DNA incubation solution overnight. After an overnight incubation, the FO-SPR sensors were washed with Tris-SDS and backfilled with 50 µM PEG-molecules in a final volume of 110 µl DNAse-free water. Finally, after 1 h incubation, the FO-SPR sensors were washed and stored in Tris-SDS.

The second strategy was based on the surface functionalization of the FO-SPR sensors described by Arghir et al. Au-coated FO-SPR sensors were functionalized with a biotin-SAM overnight, washed and stored in MES until further use. For immobilization of the biotinylated FO-SPR probes (Table 1), the FO-SPR sensors were first immersed in 0.05 mg/ml streptavidin and washed in NaOH/NaCl for 30 s. Next, the FO-sensors were incubated with 500 nM biotinylated FO-SPR probes in PBS with 270 mM NaCl, washed in NaOH/NaCl for 30 s and stored in Tris-SDS.

Example IV Ligation and Formation of AuNP-Labelled DNAzyme Substrate

Independently of the immobilization strategies described above to functionalize the FO-SPR sensors with the FO-SPR probes, the same ligation protocol was used to ligate the AuNP-probes to the FO-SPR probes, resulting in AuNP-labelled DNAzyme substrates immobilized on the FO-SPR sensor surface. First the FO- and AuNP-probes were brought together by hybridizing with a third DNA sequence or ligation template (FIG. 1I). Upon hybridization, the nick in the double stranded DNA was recognized by the ligase, which removed this nick by covalently linking the FO-SPR probes with the AuNP-probes (FIG. 1II). Once the ligase has performed its activity, it can go to a next nick and eventually perform multiple turnovers.

The ligation process was established by submerging the FO-SPR sensor for 20 min in a mixture of 1× Ampligase® reaction buffer, 0.05 u/µl ligase, different concentrations of ligation template and 2.32 nM of the functionalized AuNPs. The final reaction mixtures had a volume of 100 µl and was covered with 50 µl of Dry strip cover fluid as the ligation was performed at 50° C.

Example V DNAzyme Activity

Independently of the immobilization strategies described above, DNAzyme activity was established in the same reaction conditions. FO-SPR sensors were submerged in a reaction mixture containing 50 mM Tris buffer at pH 9.4, 150 mM NaCl, 20 mM $MgCl_2$ and different concentrations of DNAzyme (Table 1). Upon hybridization of the DNAzyme substrate arms with the DNAzyme substrate (FIG. 4I), the DNAzyme was able to cleave its substrate. Once cleaved and after dehybridization, the DNAzyme activity could be monitored due to the release of the AuNP-label (FIG. 4II). After dehybridization, the DNAzyme could recognize another substrate strand and perform its activity in multiple turnovers (FIG. 4III).

The goal of this concept is to functionalize the gold surface of a FO-SPR sensor with ssDNA, labelled with AuNPs in order to detect enzyme activity on DNA for instance DNAzyme activity. FIG. 2 illustrates the real-time monitoring of the ligation process, which was established in five steps: 1) the FO-SPR sensor was submerged in 20 mM Tris-buffer at pH 8.3 for 5 min to establish a stable baseline of the sensor, 2) the FO-SPR sensor was submerged for 20 min in the ligation mixture described above, 3) the FO-SPR sensor was again submerged in 20 mM Tris-buffer at pH 8.3 for 4 min to establish a stable baseline of the sensor, 4) the FO-SPR sensor was submerged in 10 mM NaOH washing buffer (2×30 sec) to remove all non-ligated DNA strands and 5) the FO-SPR sensor was again dipped into the Tris-buffer to quantify the FO-SPR-shift caused by the ligation process. All reaction mixtures had a volume of 100 µl and were covered with 50 µl of Dry strip cover fluid to prevent evaporation as all steps were performed at 50° C. FIG. 3 illustrates that the ligation approach can be successfully used to label the FO-SPR probes with AuNPs. FO-SPR shifts were based on the first and last baseline signal and can be controlled by changing the ligation temperature and template concentration. Increasing the template concentration up to 100 nM results in higher FO-SPR shifts, after which the signal reaches saturation. Furthermore, the specific design of the FO- and AuNP-probes plays an important role in the resulting FO-SPR shifts. As can be seen from FIG. 3, FO-SPR probe 2 reaches slightly higher FO-SPR shifts than FO-SPR probe 1, while FO-SPR probe 3 clearly reaches the highest FO-SPR shifts. Both FO-SPR probe 1 and 2 were ligated with AuNP-probe 1 using Template 1 and resulting in AuNP-labelled single stranded DNAzyme substrate of 56 bases (Table 1). While AuNP-probe 1 consisted of a $T_{10}$-spacer and random sequence to allow hybridization with Template 1, FO-SPR probe 1 and 2 were designed to contain a $T_{10}$-spacer and the full substrate sequence to be bound by the DNAzyme (Table 1). FO-SPR probe 1 and 2 only differed in their 3' modification, needed for the FO-SPR sensor surface functionalization following strategy 1 or 2 as described previously. FO-SPR probe 3, however, was modified at its 5' ending and was ligated with AuNP-probe 2 using Template 2 (Table 1). By the specific design of FO-SPR probe 3 and AuNP-probe 2, the resulting single stranded DNAzyme substrate of 56 bases was now oriented 5' to 3' from FO-SPR sensor surface to AuNP after ligation instead of 3' to 5'.

Once FO-SPR sensors could be fabricated with AuNP-labelled DNAzyme substrates, FIG. 5 illustrates that the DNAzyme activity could be monitored in real-time. The DNAzyme activity was established in four steps: 1) the FO-SPR sensor was submerged in 50 mM Tris-buffer at pH 9.4 with 150 mM NaCl and 20 mM $MgCl_2$ for 7 min to establish a stable baseline of the sensor, 2) the FO-SPR sensor was submerged for 30 min in the DNAzyme reaction mixture described above, 3) the FO-SPR sensor was submerged in 10 mM NaOH (2×30 sec) to dehybridize all DNAzyme substrate arms and remove all DNAzymes from the FO-SPR sensor surface and 4) the FO-SPR sensor was again dipped into the 50 mM Tris-buffer at pH 9.4 with 150 mM NaCl and 20 mM $MgCl_2$ to quantify the FO-SPR shift caused by the DNAzymes. All reaction mixtures had a volume of 100 µl and were covered with 50 µl of Dry strip cover fluid to prevent evaporation as all steps were performed at 55° C. FIG. 6 than demonstrates that FO-SPR shifts associated with DNAzyme activity could be distinguished from a control for all three FO-SPR probes. The FO-SPR shifts were based on the first and last baseline signal and confirm that the more FO-SPR probes are labelled with a AuNP through ligation, the higher the output signal of the DNAzyme. FO-SPR probe 2 shows slightly higher FO-SPR shifts than FO-SPR probe 1, while FO-SPR probe 3 clearly shows the highest FO-SPR shifts (FIG. 7). In addition to the differences in FO-SPR probes discussed previously, the specific design of FO-SPR probe 3 placed the nick to be ligated within the sequence that is bound by the DNAzyme (Table 1), making FO-SPR probe 3 and AuNP-probe 2 only partial complementary to the DNAzyme substrate arms. Placing this nick within the sequence to be bound by the DNAzyme could improve the selectivity of the DNAzyme towards ligated DNAzyme substrates and contribute to a better efficiency of the DNAzyme.

Real-Time FO-SPR Monitoring of DNAzyme Activity

DNAzyme reaction mixtures contained 1×DNAzyme reaction buffer and 0, 0.1, 1, 3.125, 6.250, 10, 12.5, 25, 50 or 100 nM DNAzyme. A first baseline was established in 1× DNAzyme reaction buffer for 7 min, followed by incubation of the FO-SPR sensors in one of the DNAzyme reaction mixtures for 30 min. The catalytic reaction was stopped by washing two times 30 s with 10 mM NaOH, one time 30 s with TE buffer and afterwards a second baseline was recorded in the 1×DNAzyme reaction buffer. All reaction vials were heated together at 55° C. and were covered with mineral oil.

DNAzyme Inactivation With Blocker Strand

Different concentrations of 100, 140 or 180 nM inhibitor strand were mixed in 1× DNAzyme reaction buffer with a fixed DNAzyme concentration of 100 nM. After 30 s heating at 95° C. and incubation at 55° C. for 30 min, the inhibitor-DNAzyme complex was cooled and stored at 4° C. DNAzyme inhibition experiments were performed identically to the DNAzyme activity experiments, but instead of different DNAzyme concentrations, the FO-SPR sensors were incubated with a four-time dilution of the different DNAzyme-inhibitor mixtures in 1×DNAzyme buffer.

DNAzyme-Based Target Detection

Target concentrations of 0, 10, 12.5, 15, 20, 25 or 30 nM ssDNA were incubated at 55° C. for 20 min in 1×DNAzyme reaction buffer together with a 1.4:1 ratio of inhibitor-DNAzyme complex prepared as aforementioned, prior to starting the DNAzyme activity read-out. Read-out of the DNAzyme activity was performed identical as described earlier, except for the first baseline. This baseline was prolonged to 10 min, making a total of 30 min incubation of the ssDNA target with the DNAzyme-inhibitor complex before starting the read-out.

Scanning Electron Microscopy (SEM) Images and Data Analysis

High resolution scanning electron microscopy (SEM) images were made with a FEI Nova Nanosem 450 (The Thermo Fisher Scientific group—FEI, Hillsboro, USA). Visualization of the 20 nm AuNPs was established with a backscatter detector (CBS, concentric backscatter detector) using an acceleration voltage of 4.5 kV in the column and a magnification of 100,000. Applying a bias of 4 kV on the stage enabled beam deceleration, resulting in a landing energy of 500 V. To obtain stable imaging, drift corrected frame integration (DCFI) was used. The difference in contrast of the images could be explained by small differences in the sample preparation and different position of the image on the FO-SPR sensor surface. Quantification of the AuNPs was done by using ImageJ 1.48v (National Institutes of Health, Bethesda, USA) 52, a Java-based image-processing program. For every condition with images with a surface area of 7.5 µm2 were sharpened if needed and after setting the proper noise tolerance, the AuNPs could be counted using the 'Find Maxima' tool in ImageJ. For every condition, the AuNP-density was determined for three images at different locations on the same fiber.

FO-SPR data were recorded with LabView (National Instruments, Austin, USA) and further processed using Matlab 2015b (The MathWorks Inc., Natick, USA). The FO-SPR signals were normalized by subtraction of the initial average baseline and different steps were distinguished within both the ligation an DNAzyme activity sensorgrams. Different parameters were defined to enable statistical analysis with JMP®13 (SAS Institute Inc., Cary, USA): (i) hybridization shift, (ii) ligation shift, (iii) DNAzyme shift, (iv) ligation efficiency, (v) DNAzyme efficiency and (vi) half time value. Significant differences were analyzed by performing one-way ANOVA followed by Tukey multiple comparison with an α-level of 0.05. Calibration curves were linearly fitted by y=a x+b, with y the logarithmic half-life values, x the logarithmic concentration variable, a the slope and b the intercept. The limit of detection (LOD) was based on the linear regression and calculated as LOD=3×σ/S, with σ the standard deviation of the response, estimated by the root mean squared error (RMSE) and S the slope of the calibration curve.

Principle of the Designed FO-SPR Sensor and DNA Target Detection With DNAzyme Inhibitor The ligation strategy to functionalize the FO-SPR sensor with AuNP-labelled substrates is depicted in FIG. 8A. Three DNA probes are used to perform the ligation: (i) a 5'-thiolated FO-SPR probe immobilized on the FO-SPR sensor surface, (ii) a 3'-thiolated AuNP-probe immobilized on the AuNP-surface and (iii) a ligation template partially complementary to both the FO-SPR and AuNP-probe. Upon hybridization of the FO-SPR and AuNP-probe with the ligation template, the ligase recognizes the nick in the double DNA strand and links the 5'-phosphorylated AuNP-probe with the FO-SPR probe by a NAD-dependent ligation. As a result, AuNP-labelled DNAzyme substrates are formed. AuNP-labels are well-known to significantly amplify the FO-SPR response signals54 and are introduced here to enable real-time direct monitoring of the DNAzyme cleavage activity. Furthermore, the FO-SPR and AuNP-probes are designed in such a way that both DNA oligos each contain a part of the DNAzyme substrate, eliminating DNAzyme cleavage of unlabeled substrates. FIG. 8B illustrates the DNAzyme-based target detection, using the designed FO-SPR sensor. The system includes three additional DNA oligos: (i) a synthetic, specific DNA target, (ii) a DNAzyme and (iii) a ssDNA inhibitor. The inhibitor is designed to block the DNAzyme by partial hybridization. It contains a loop of 22 nucleotides, which can be adapted to any target without changing the DNAzyme sequence. In presence of the target, the inhibitor preferentially binds the DNA target of interest due to higher complementary and therefore resulting in a lower ΔG compared to the interaction with the DNAzyme. This way, the DNAzyme is activated and can start cleaving the AuNP-labelled substrate on the FO-SPR sensor.

Optimization Ligation Temperature and Template Concentration

AuNP-labelling of the immobilized FO-SPR probes depends on the ligation template concentration, the functionalized AuNP concentration, the amount of ligase, the incubation temperature and time. Together these parameters determine the available number of nicks for the ligase, formed by hybridization between the template and FO-SPR and AuNP-probes. Both the ligation temperature and template concentration were studied in more detail, while the functionalized AuNP concentration, incubation time and amount of ligase were fixed based on previous work of Knez (Ref 1 and 2) and the Ampligase product specifications. FIG. 9A shows the real-time normalized FO-SPR signal of the ligation process, which consists of four different steps. Step 1 represents a first stabilization step, which enables the FO-SPR sensor to reach its baseline level. Initial signal drift is caused by a change in refractive index (RI) going from air to buffer and the increasing temperature, as the FO-SPR sensor is temperature sensitive. In step 2, AuNP-labelling of the FO-SPR probes takes place by ligation (FIG. 8A) and the increasing FO-SPR shift follows mainly from AuNP hybridization to the FO-SPR sensor surface. Hybridization shifts were determined as the difference between the start- and endpoint of this second step. Step 3 represents a washing step in Tris buffer and two times in NaOH, clearly distinguishable by the short RI changes in air when switching reaction vials. Finally, step 4 corresponds to a second stabilization step, which enables the FO-SPR sensor to reach a new baseline level in the identical conditions of step 1. The difference between both baselines (step 1 and step 4 respectively) was defined as the ligation shift, as hybridized AuNPs where no ligation took place were only washed away after step 3.

Since the ligase performs better at higher temperatures, successful ligation is strongly dictated by the hybridization events of the ligation template. Therefore, both hybridization and ligation shifts were first evaluated for three different temperatures, while keeping the ligation template concentration constant. As can be seen from FIG. 9B, the hybridization shifts did not change significantly (P=0.3) by increasing the temperature from 50 to 55° C., but decreased significantly (P<0.0001) at 60° C. This is explained by the fact that at 60° C. the reaction conditions are approaching the melting temperature (Tm) of the ligation template, being 65.1±0.3° C. The ligation shifts were found to increase from 50 to 55° C., followed by a decrease at 60° C. (P<0.01). As the ligase's activity increases with temperature, an increasing ligation shift could be expected, however also here the decrease at 60° C. could be explained by approaching the Tm of the ligation template. Optimal ligation conditions would result in both a large, equal hybridization and ligation shift, meaning that all hybridized AuNPs have been ligated to the FO-SPR sensor surface. By taking the ratio of the hybridization and ligation shift for each of the temperatures, ligation efficiencies were determined as a function of temperature (FIG. 9C). The ligation efficiency increased up to 55° C. (P≤0.0002), after which an efficiency of 90% was reached and no further increase was observed (P=0.06). Based on the large hybridization shift, maximal ligation shift of 101.5±2.1 nm and ligation efficiency of 90.0±1.0%, 55° C. was regarded as the optimal temperature and selected for all further experiments. Compared to the typical range of FO-SPR shifts around 10 nm previously reported (3, 4, 5), the size of the maximal obtained FO-SPR shifts here are more than 10-fold higher. This can be explained by using relatively short DNA oligos, a higher AuNP concentration and the specific choice of incubation time and reaction temperature in order to improve and maximize FO-SPR parameters such as the FO-SPR shift, the dynamic range and the LOD. Furthermore, optimization of the ligation template concentration is visualized in FIG. 10. Hybridization shifts, ligation shifts and ligation efficiencies were monitored in real-time (data not shown) and determined for 0, 10, 100 and 1000 nM ligation template. For both hybridization as well as the ligation shifts (FIG. 10A), the response signal was significantly lower at 10 nM template compared to the higher template concentrations (P<0.0001). Further increase of the template concentration enabled more AuNPs to bind the FO-SPR sensor and eventually reach a saturation level on the FO-SPR sensor, which is determined by the geometry and steric interactions of the AuNPs under specified reaction conditions. For both the hybridization and ligation shifts the response signal increased up to 100 nM template, after which the signal remained constant (P>0.3). In addition, ligation of the AuNPs to the FO-SPR sensor surface was evaluated with high resolution SEM images. FIG. 10C shows part of the SEM images made for every ligation condition using a different ligation template concentration. In case of 0 nM ligation template, aspecific binding to the FO-SPR sensor surface caused few AuNPs to be observed, resulting in a AuNP-density of 5±6 particles/$\mu m^2$ by counting the AuNPs in the SEM images. Furthermore, the SEM image shows the gold islands of the sputtered thin film (6). By increasing the ligation template concentration, an increasing amount of AuNPs ligated to the FO-SPR sensor surface is observed in the SEM images. The obtained AuNP-densities were 244±31 particles/$\mu m^2$, 666±56 particles/$\mu m^2$ and 678±95 particles/$\mu m^2$ for 0, 10, 100 and 1000 nM ligation template, respectively. Based on the SEM images, controlling the AuNP-density with the ligation template and saturation of the AuNP binding at 100 nM template concentration was confirmed (P=1). FIG. 10B represents the ligation efficiencies, which showed no significant difference with template concentration (P>0.2) and a maximal value of 90.3±1.4% was obtained at 100 nM template. Therefore, a template concentration of 100 nM was set as an optimum and together with the optimal temperature of 55° C. used in all further experiments.

FO-SPR Characterization of DNAzyme Activity

In previous section, optimal ligation conditions were obtained to functionalize the FO-SPR sensor surface with AuNP-labelled DNAzyme substrate sequences. In this section, potential DNAzyme activity was studied by incubation of the FO-SPR sensors with a DNAzyme. In this study, the 10-23 DNAzyme was preferred, based on several of its characteristics as mentioned in the introduction (7, 8, 9). Real-time monitoring of the FO-SPR response enabled to quantify the FO-SPR shift caused by substrate cleavage and release of AuNPs. In addition, the reaction speed could be studied by determining the half-life value of the FO-SPR sensor response. Moreover, in combination with the ligation shifts as determined in previous section, the DNAzyme efficiency could be described. FO-SPR sensors with AuNPs were incubated with DNAzyme concentrations in a range from 0-100 nM and the corresponding real-time sensorgrams for five DNAzyme concentrations are illustrated in FIG. 11A. Furthermore, SEM images were made of three different FO-SPR sensors after 0, 5 and 15 min incubation with 25 nM DNAzyme (FIG. 11B). The SEM images confirm the release of AuNPs by incubation with the DNAzyme over time. Based on the AuNP-count of the SEM images, the initial AuNP-density was 607±28 particles/$\mu m^2$, which decreased to 432±26 particles/$\mu m^2$ after 5 min and 89±4 particles/$\mu m^2$ after 15 min. In addition, DNAzyme shifts were defined as the difference between both baselines and DNAzyme efficiencies as the ratio of DNAzyme and ligation shift. After all, the ligation shift gives the maximal shift that can be expected after incubation with the DNAzyme. Both parameters showed an increasing, logarithmic trend with the DNAzyme concentration up to 12.5 nM of DNAzyme, after which the DNAzyme shift saturated, giving a dynamic range of one decade. However, based on the real-time monitoring feature of the FO-SPR sensor, half-life values of all response signals, except for 0 nM DNAzyme, were determined as a kinetic parameter to study the effect of the different DNAzyme concentrations. Determination of the half-life values improved the dynamic range and moreover could avoid the need of both baselines, used to calculate the endpoint DNAzyme shifts. Theoretically, 0 nM DNAzyme has an infinite half-life value, but the experimental half-lives showed on average low values, which are determined by the smallest drift in the FO-SPR signals and not by any DNAzyme activity. Therefore, the half-life value of 0 nM DNAzyme was not used in the study of the data. Initially, the half-life values remained constant up to 3.125 nM, followed by an exponential decreasing trend. In FIG. 12, a logarithmic transformation of the exponential part was plotted in function of the logarithmic DNAzyme concentrations and a linear calibration curve was obtained ($R^2$ of 0.95) with a RMSE of 0.07. Based on the linear regression, the LOD was 2.3 nM.

Optimization Inhibitor Concentration for DNAzyme Inactivation

To retain a controlled catalytic activity, DNAzyme blocking was established through partial DNA hybridization. The inhibitor strand was designed to be complementary to the DNAzyme's binding arms and part of the catalytic core, except for four nucleotides. In addition, one of the blocking regions lacked complementarity with the outer nucleotide of the binding arm and the other blocking region contained a G-T wobble structure (9). This way, the inhibitor strand with internal loop was calculated to have a $T_m$ enabling hybridization to the DNAzyme under DNAzyme reaction conditions and dehybridization only by a specific trigger (The DINAmelt Web Server (10,11)). Formation of the duplex between DNAzyme and inhibitor strand was confirmed qualitatively with gel electrophoresis prior to the FO-SPR experiments.

The degree of DNAzyme blocking is steered by the ratio between the inhibitor strand and the DNAzyme. Moreover, there is a tradeoff between the excess of inhibitor and the sensitivity of the assay. Since in the final biosensing concept the inhibitor needs to interact with the target of interest, the excess of inhibitor strands should be minimized. In order to moderate the increase of the inhibitor excess but still reach a maximal DNAzyme shift, 25 nM DNAzyme was chosen as the concentration to study the FO-SPR shifts in function of different DNAzyme-inhibitor ratios. FIG. 13 presents the FO-SPR shifts obtained for a 1:1, 1.4:1 and 1.8:1 ratio of inhibitor strands and DNAzyme. In comparison with the positive control, not containing any inhibitor, the presence of the inhibitor strand in a 1:1 ratio reduced the FO-SPR shift more than 50%. Further increase of the inhibitor-DNAzyme ratio resulted in FO-SPR shifts comparable to the negative control, only containing 200 nM inhibitor strand. Therefore, minimal background and inhibitor excess were realized with a ratio of 1.4:1 inhibitor strand and DNAzyme (used in further experiments).

DNAzyme-Based Detection of a Synthetic DNA Target

Strand displacement (12) was used as the mechanism for target specific signal generation. The internal loop built into the inhibitor strand enables great flexibility towards the target. Whereas the blocking regions were designed to assure blocking of the DNAzyme, the internal loop was designed to enable preferential binding of the inhibitor to the target due to its higher complementarity with the target compared to the DNAzyme. This target-triggered release of the DNAzyme was first confirmed qualitatively with gel electrophoresis.

Specific target detection was explored using the same reaction conditions as applied for the real time DNAzyme activity, however this time the DNAzyme was added as a blocked complex with the inhibitor strand as described in previous section. DNAzyme shifts and efficiencies, triggered by different target concentrations, were determined for all response signals as mentioned earlier. Based on the half-life values obtained for 0, 10, 12.5, 15, 20, 25 and 30 nM of target DNA, a calibration curve was established. Both the DNAzyme shifts and DNAzyme efficiencies increased with elevated target concentrations. In contrast to the DNAzyme-only experiments, a sigmoidal trend was observed. We hypothesize that the inhibitor excess, needed to assure complete DNAzyme blocking, caused the initial lag in signal generation. Furthermore, the FO-SPR shifts saturated from 15 nM DNA target onwards. Therefore, half-life values of the FO-SPR response signals were determined and a log-log transformation was performed similar to the DNAzyme-only results (FIG. 12). Based on the log-log transformation of the half-life values, the kinetic information within the response signal was used to improve and increase the dynamic range compared to the use of the endpoint DNAzyme shifts. The logarithm of the half-life values was observed to decrease linearly ($R^2$=0.94) with the logarithmic target concentration (FIG. 14). An RMSE of 0.08 was obtained and the LOD was calculated to be 1.4 nM. Based on these results, we demonstrated the potential of a user friendly, innovative DNAzyme-based FO-SPR biosensor for the specific detection of DNA biomarkers. In further research, the FO-SPR sensor could be extended towards different types of RNA-cleaving nucleic acid enzymes and amplification cascades to improve the sensitivity and broaden the dynamic range. In addition, coupling of the DNAzyme cleavage activity with aptamers would also make the system suitable for the detection of other target molecules.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 17 explains and displays a first DNA probe (4) covalently bound to the surface (19), of a solid carrier for instance a magnetic, glass, micro- or macro-object, a microcarrier or a microbead and second DNA probe (5) covalently bound to the metallic nanoparticle or a metallic nanoparticle cluster (9) is ligated with ligation template (6) and the ligation enzyme (8) into single strand DNA probe (7) between the solid separable surface (19) and the or metallic nanoparticle cluster (9) whereby the single strand DNA probe (7) incorporates or comprises the NAzyme substrate (12) for a selected NAzyme. The ligation zone (18) in between the first DNA probe (4) and the second DNA probe (5) is situated within the NAzyme substrate (12) hybridized or hybridizable to the NAzyme (17). In step 1 the Nazyme substrate complex (25) is formed. In step 2 activated Nazyme hybridizes to the Nazyme substrate complex (25) and cleaves the single strand DNA probe at the cleavage point (20). The cleaved off DNA probe (21) covalently bound to the metallic nanoparticle or a metallic nanoparticle cluster (9) bears a specific single strand DNA sequence. In step 3 the cleaved off DNA probe (21) covalently bound to the metallic nanoparticle or a metallic nanoparticle cluster (9) hybridizes to a single strand DNA probe (22) covalently bound to the sensing surface (2) resulting in an increased signal. By increasing the temperature in step 4 the hybridized cleaved off DNA probe (21) covalently bound to the metallic nanoparticle or a metallic nanoparticle cluster (9) will dehybridize or melt off the complementary single strand DNA probe (22) covalently bound to the sensing surface (2) resulting in a drop in the signal (A) at a specific temperature related to the cleaved off DNA probe (21) sequence.

Figure 1:
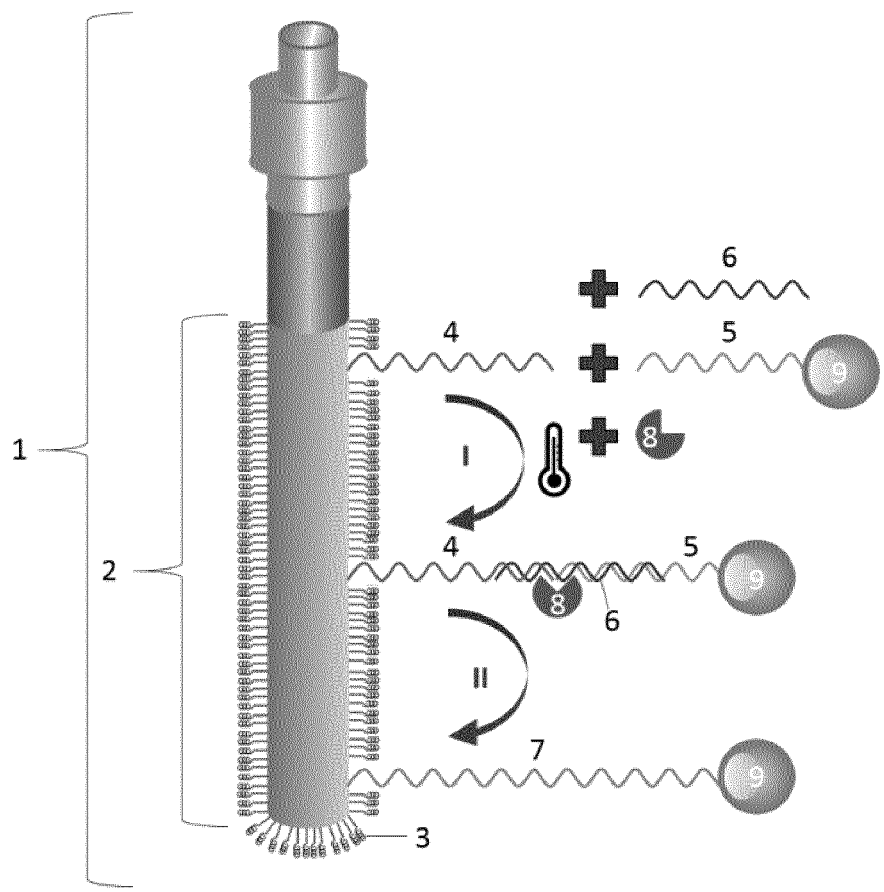
FIG. 1 shows a schematic overview of the prefunctionalized FO-SPR sensor. Both the FO-SPR sensor and AuNPs surfaces were functionalized with ssDNA (FO-SPR or AuNP-probe) and backfilled with PEG-molecules prior to ligation. In step I both the immobilized FO- and AuNP-probe are mixed together to form one complex upon hybridization to the ligation template. Upon recognition of the nick by the ligase in step II, the FO-SPR and AuNP-probe are ligated together to construct a AuNP-labelled DNAzyme substrate. 1) is the FO-SPR sensor, 2) is the sensing surface, 3) are PEG-molecules, 4) is FO-SPR nucleotide probe, 5) is AuNP-nucleotide probe, 6) is ligation template, 7) is ligated FO- and AuNP-nucleotide probe, 8) is ligase and 9) is gold nanoparticle.
Figure 2:
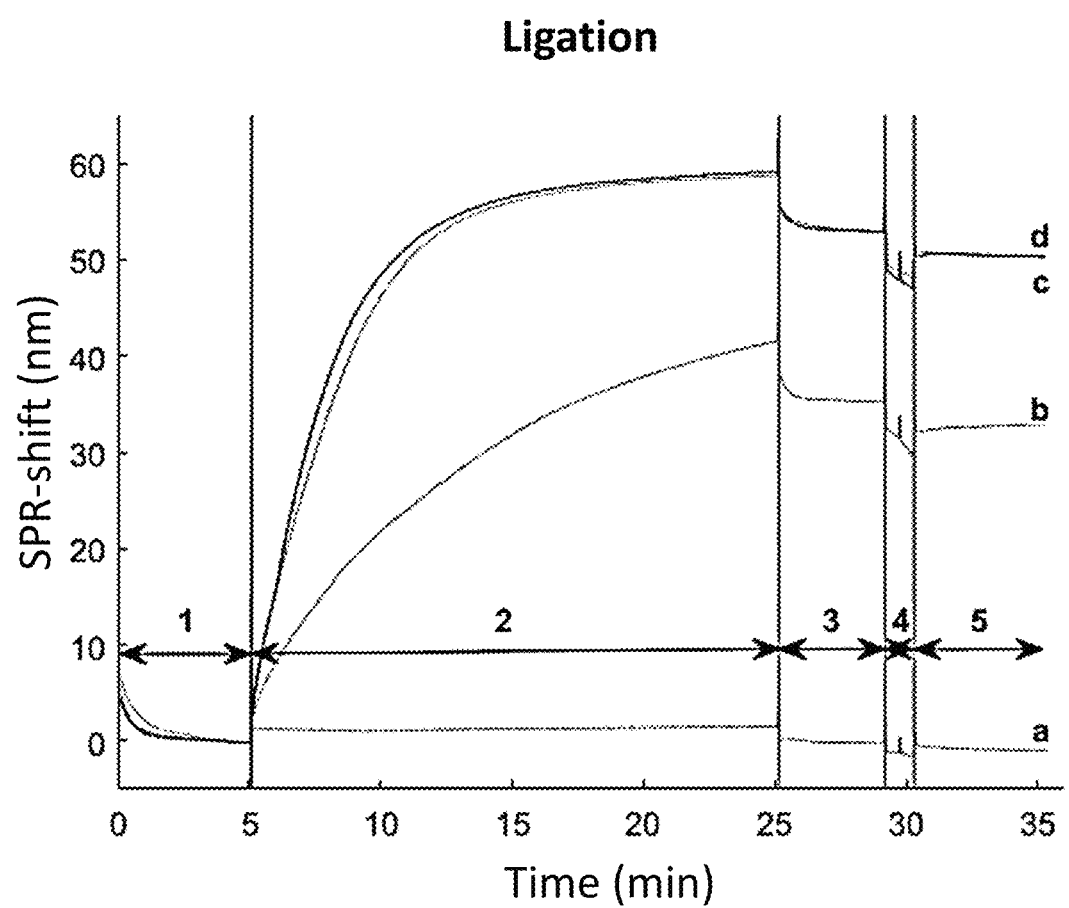
FIG. 2 illustrates the formation of the hybridization complex and the ligation process in real-time for FO-SPR sensors functionalized with FO-SPR probe 1 and using different ligation template concentrations. Every measurement included five different steps: 1) baseline stabilization before ligation, 2) hybridization complex formation and ligation, 3) baseline stabilization after ligation, 4) washing steps and 5) baseline stabilization after washing. Similar measurements were obtained for FO-SPR sensors using FO-SPR probe 2 and 3, but are not shown. a) is 0 nM Template, b) is 10 nM Template, c) is 100 nM Template and d) is 1 µM Template.
Figure 3:
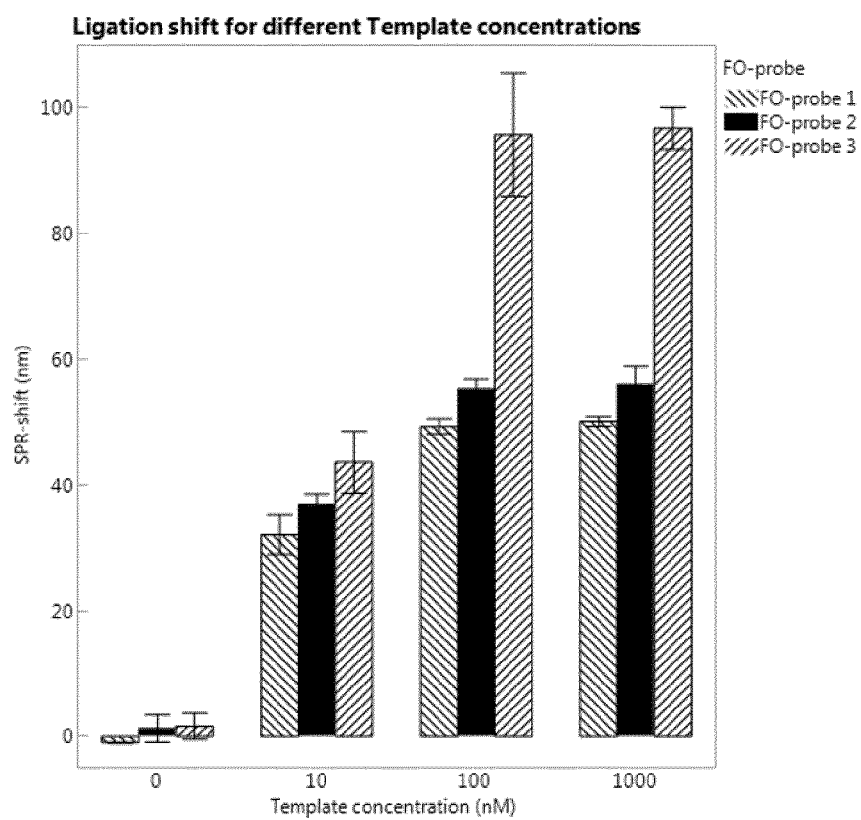
FIG. 3 presents the FO-SPR shifts in function of ligation template concentration associated with the ligation process of FO-SPR sensors functionalized with one of the FO-SPR probes listed in Table 1. FO-SPR signals were normalized and consequently FO-SPR shifts were calculated based on the first and last baseline.
Figure 4:
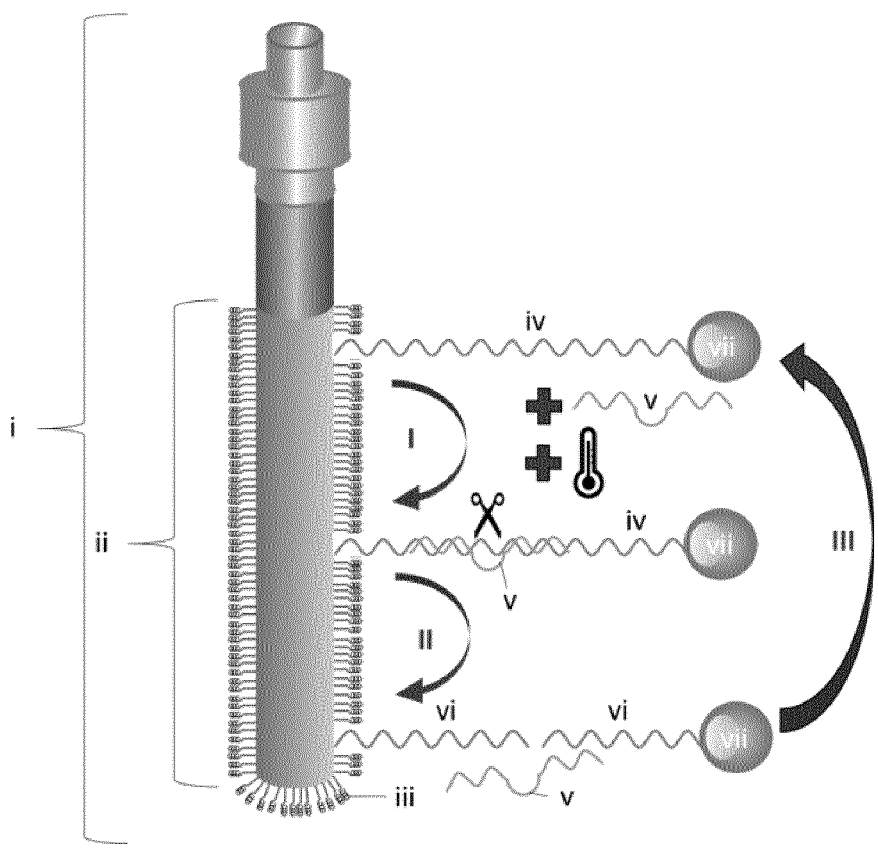
FIG. 4 shows a schematic overview of the DNAzyme activity. Once prefunctionalized with AuNPs, the FO-SPR sensors were incubated with DNAzymes. In step I, a AuNP-labelled DNAzyme substrate is recognized by the DNAzyme through hybridization. Upon recognition, the DNAzyme performs its cleavage activity in step II and releases a AuNP by dehybridization. Once dehybridized, the DNAzyme can bind a next substrate as illustrated in step III. The legends refer to the following components: i) the FO-SPR sensor, ii) the sensing surface, iii) the PEG-molecules, iv) the DNAzyme substrate, v) the DNAzyme, vi) the cleaved DNAzyme substrate and vii) the gold nanoparticle.
Figure 5:
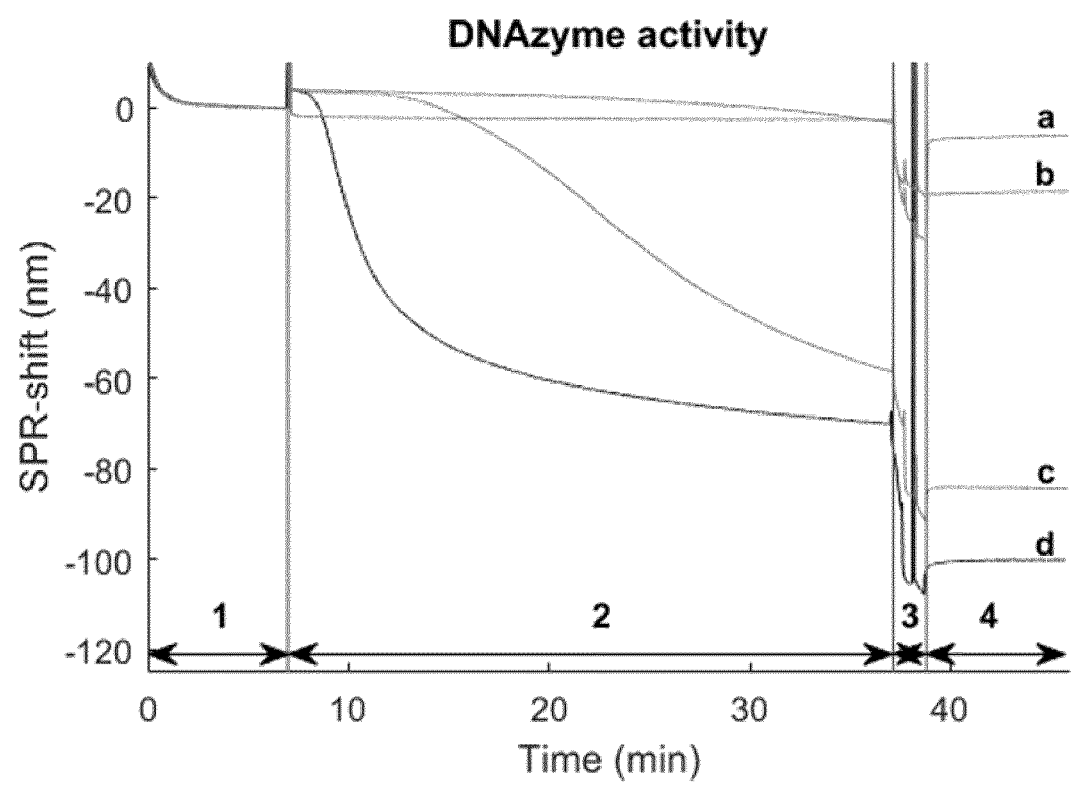
FIG. 5 illustrates the DNAzyme activity measurements in real-time for a control (DNAzyme reaction mixture without any DNAzyme present) and three different DNAzyme concentrations. Every measurement included four different steps: 1) baseline stabilization before sample measuring, 2) sample incubation, 3) washing steps and 4) baseline stabilization after sample measurement. The legends refer to the following: 0 nM DNAzyme, 1 nM DNAzyme, 10 nM DNAzyme and 100 nM DNAzyme.
Figure 6:
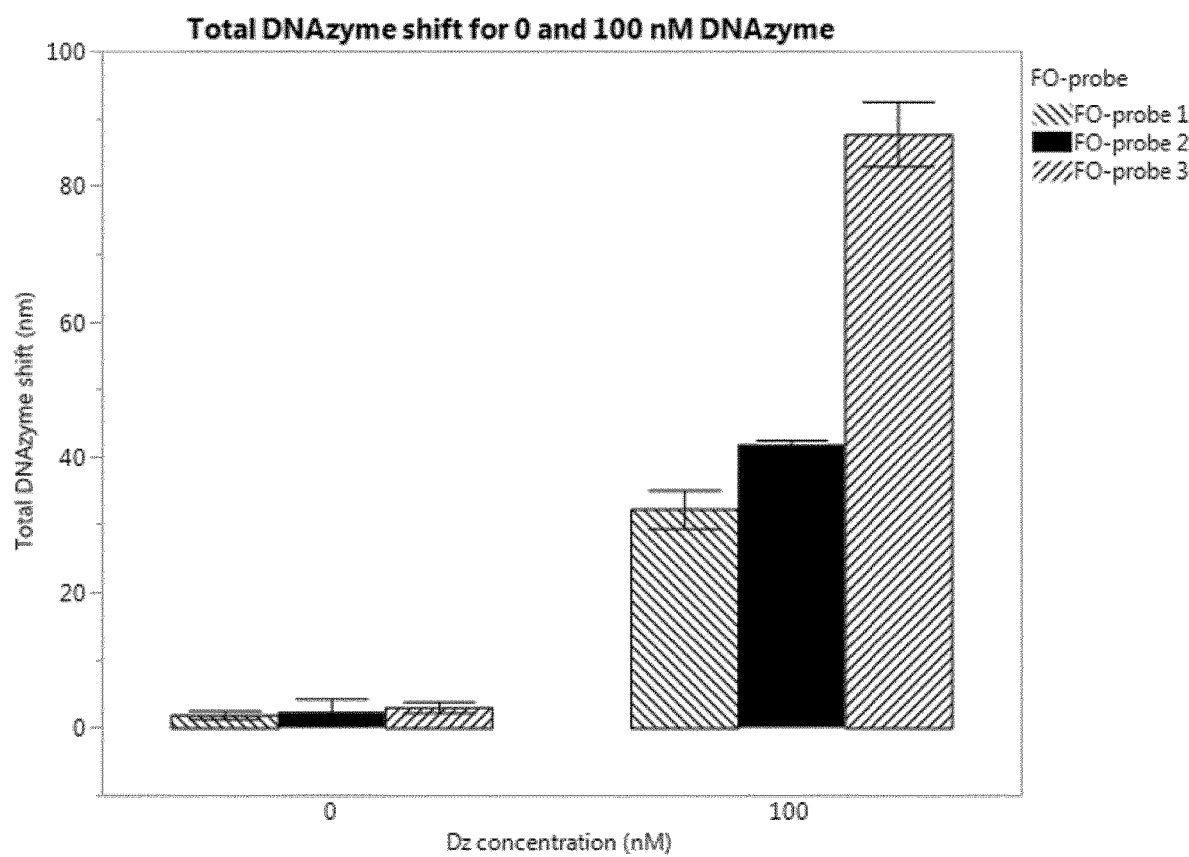
FIG. 6 presents the FO-SPR shifts associated with the DNAzyme activity of a control (DNAzyme reaction mixture without any DNAzyme present) and 100 nM DNAzyme for FO-SPR sensors functionalized with one of the FO-SPR probes listed in Table 1. FO-SPR signals were normalized and consequently FO-SPR shifts were calculated as the difference between baselines.
Figure 7:
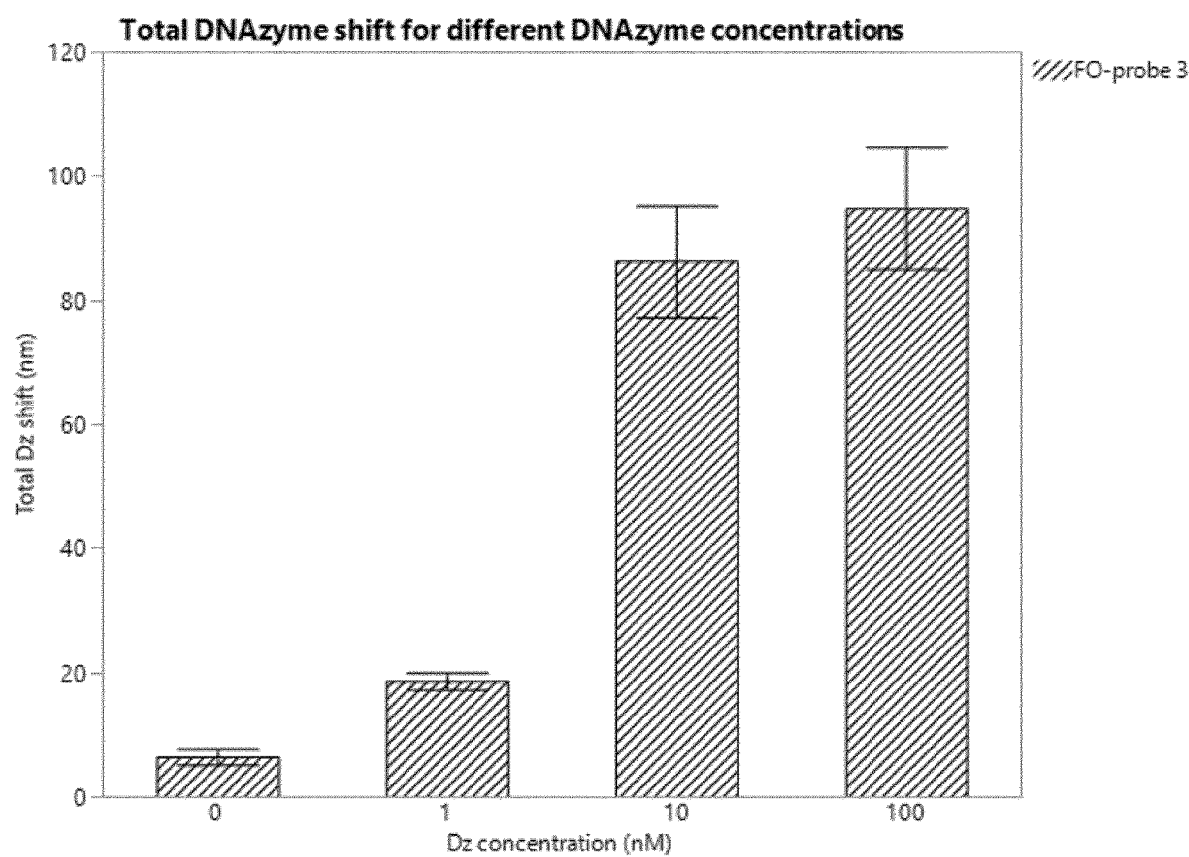
FIG. 7 presents the FO-SPR shifts in function of different DNAzyme concentrations for FO-SPR sensors functionalized with FO-SPR probe 3. FO-SPR signals were normalized and consequently FO-SPR shifts were calculated as the difference between baselines.
Figure 8:
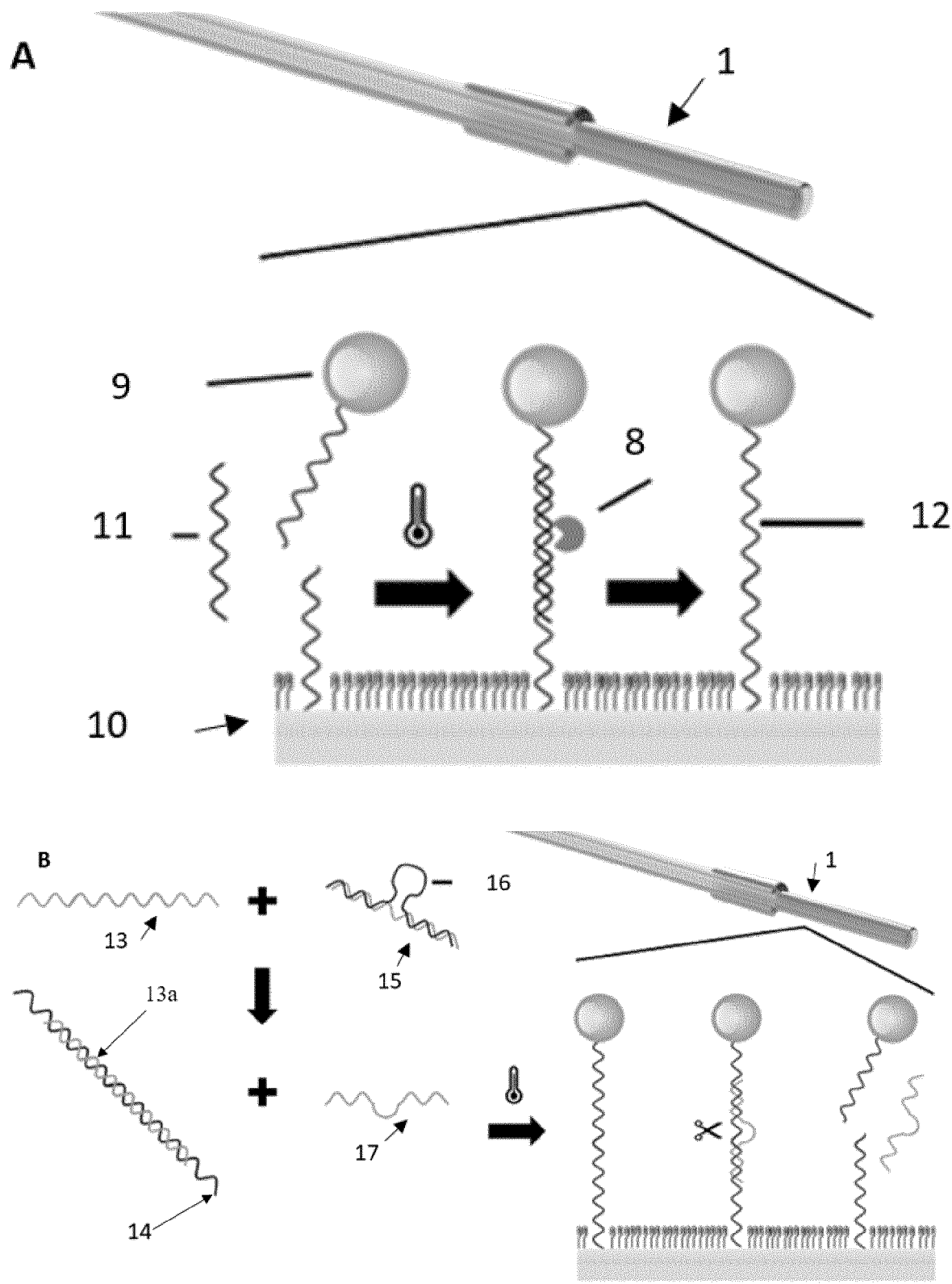
FIG. 8. Provides an illustration of (A) the ligation strategy and (B) the DNAzyme-based target detection. The following number legend are used to mark the different components 1) is the FO-SPR sensor, 8) is ligase, 9) is gold nanoparticle, 10) is gold surface on glass fiber, 11) is DNA template, 12) is NAzyme substrate, 13) is target, 13a) bound target 14) is inhibitor strand, 15) blocked NAzyme, 16) is the inhibitor strand with internal loop for target detection, 17) is NAzyme FIG. 9 displays optimization of the ligation temperature. A) Real-time normalized FO-SPR shifts for 3 different ligation temperatures are presented. Every measurement consisted of 4 steps: 1) first baseline, 2) hybridization and ligation, 3) washing and 4) second baseline; B) represents the hybridization and ligation shifts (filled and shaded bars respectively) and C) represents the ligation efficiency or ratio of the ligation and hybridization shifts. Error bars represent one standard deviation (n=4).
Figure 9:
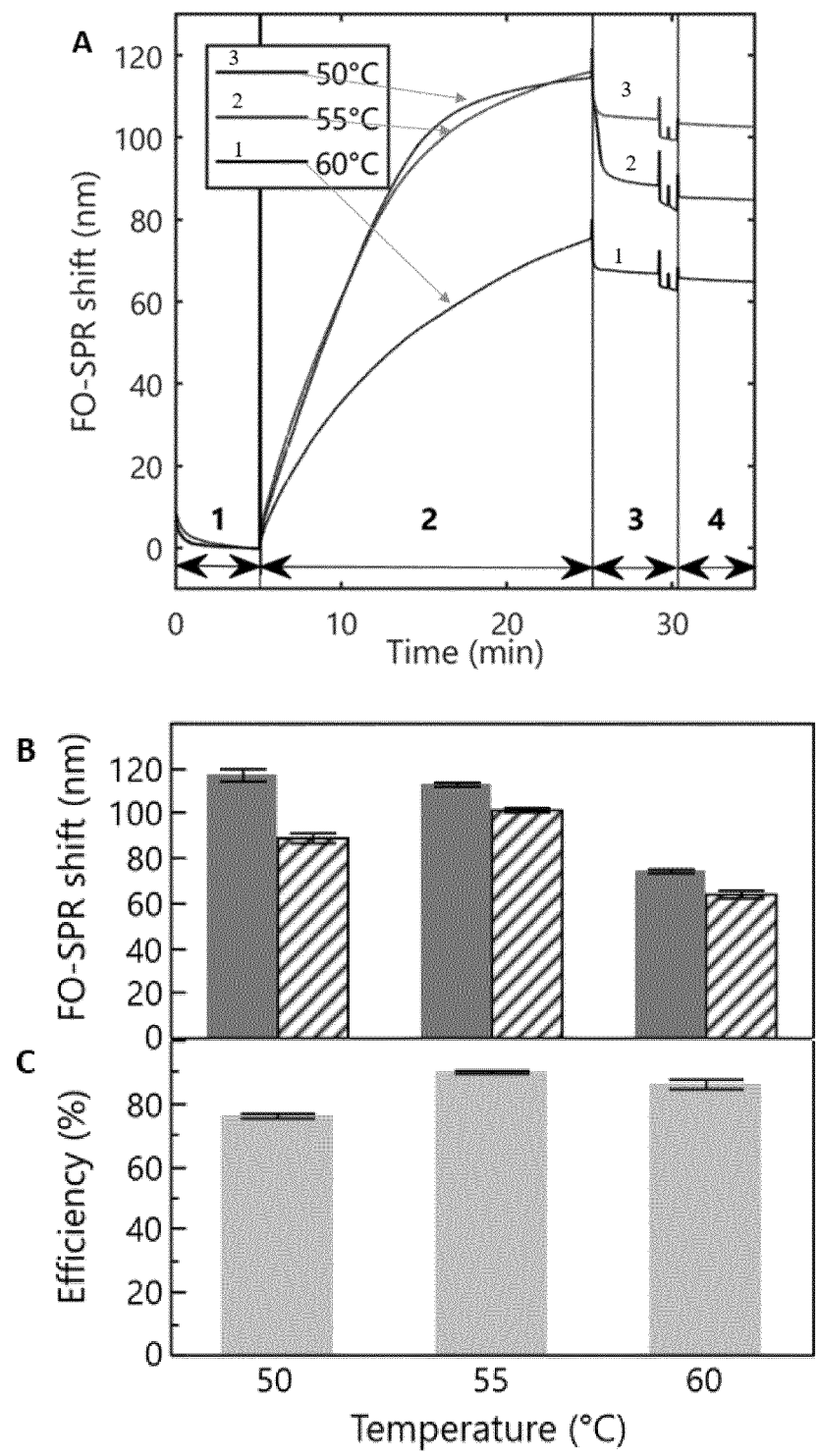
Figure 10:
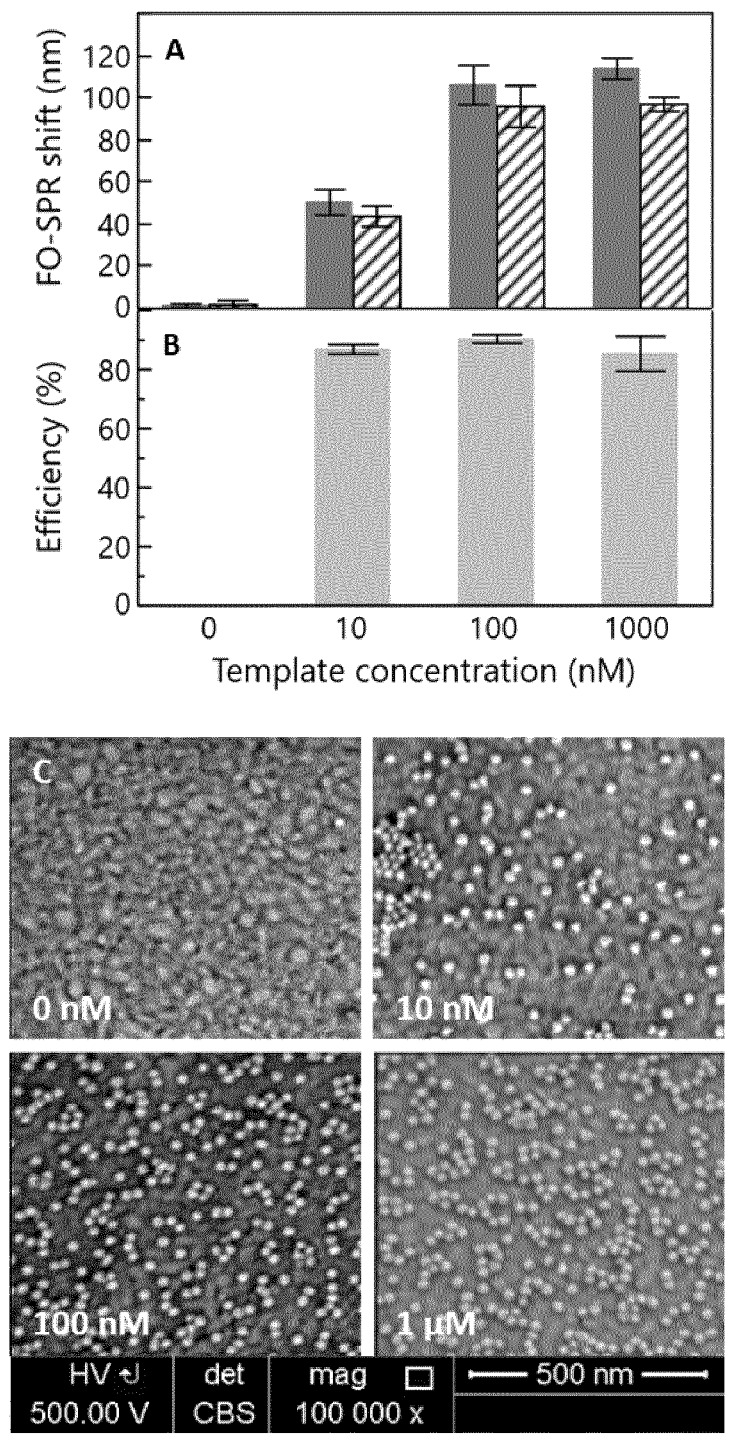
FIG. 10 demonstrates the optimization of the ligation template concentration. A) represents the hybridization and ligation shifts (filled and shaded bars respectively), while B) represents the ligation efficiency. Error bars represent one standard deviation (n=4). C) shows SEM images of 4 different FO-SPR sensors after ligation with 0, 10, 100 and 1000 nM ligation template.
Figure 11:
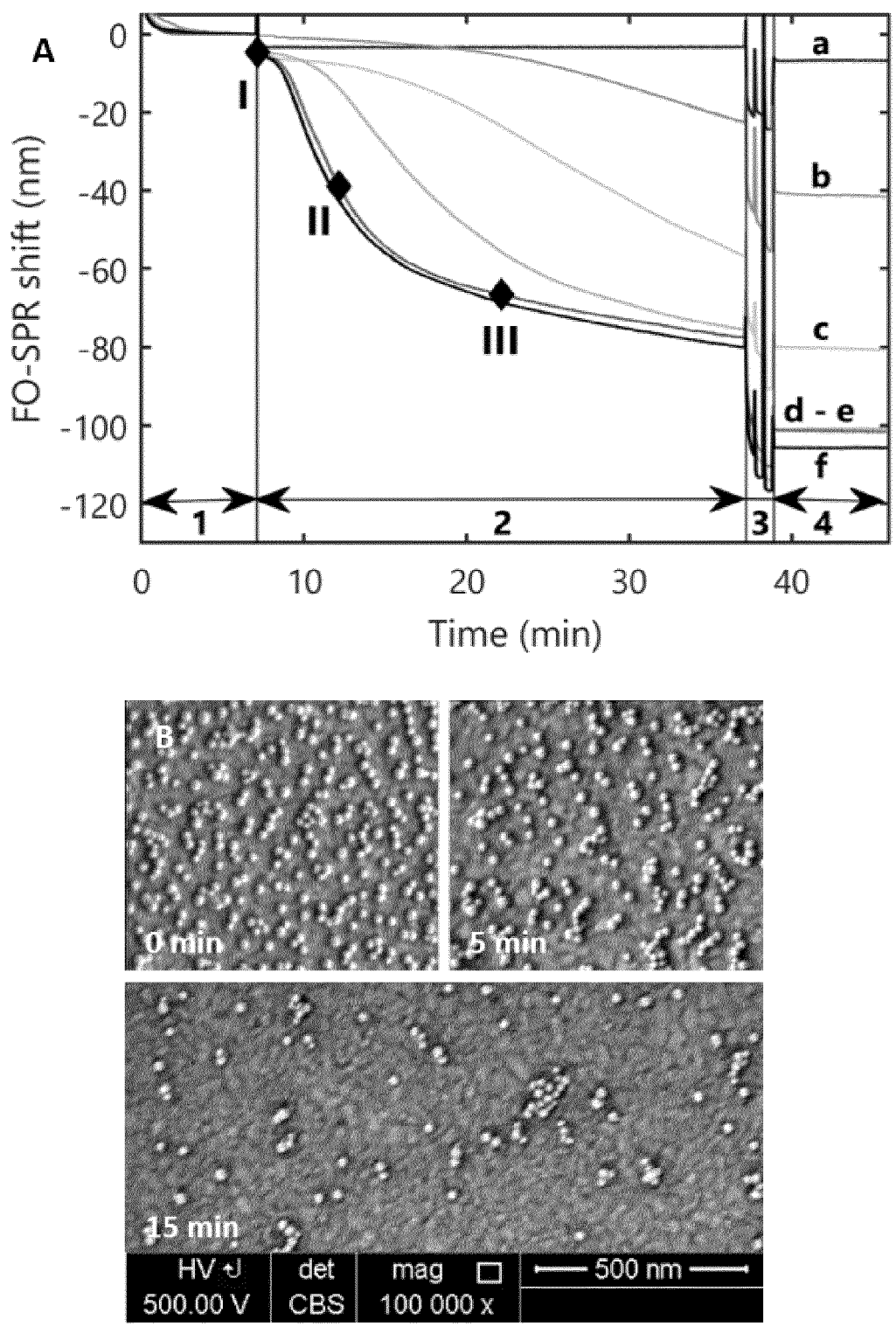
FIG. 11 demonstrates the real-time DNAzyme FO-SPR response. A) Real-time normalized FO-SPR shifts for 6 different DNAzyme concentrations are presented: a) 0 nM, b) 3.125 nM, c) 6.25 nM, d) 12.5 nM, e) 25 nM and f) 50 nM. Every measurement consisted of 4 steps: 1) first baseline, 2) DNAzyme incubation, 3) washing and 4) second baseline and B) represents the SEM images taken after I) 0 min, II) 5 min and III) 15 min of incubation with 25 nM DNAzyme. The time spots were also indicated on figure A (♦).
Figure 12:
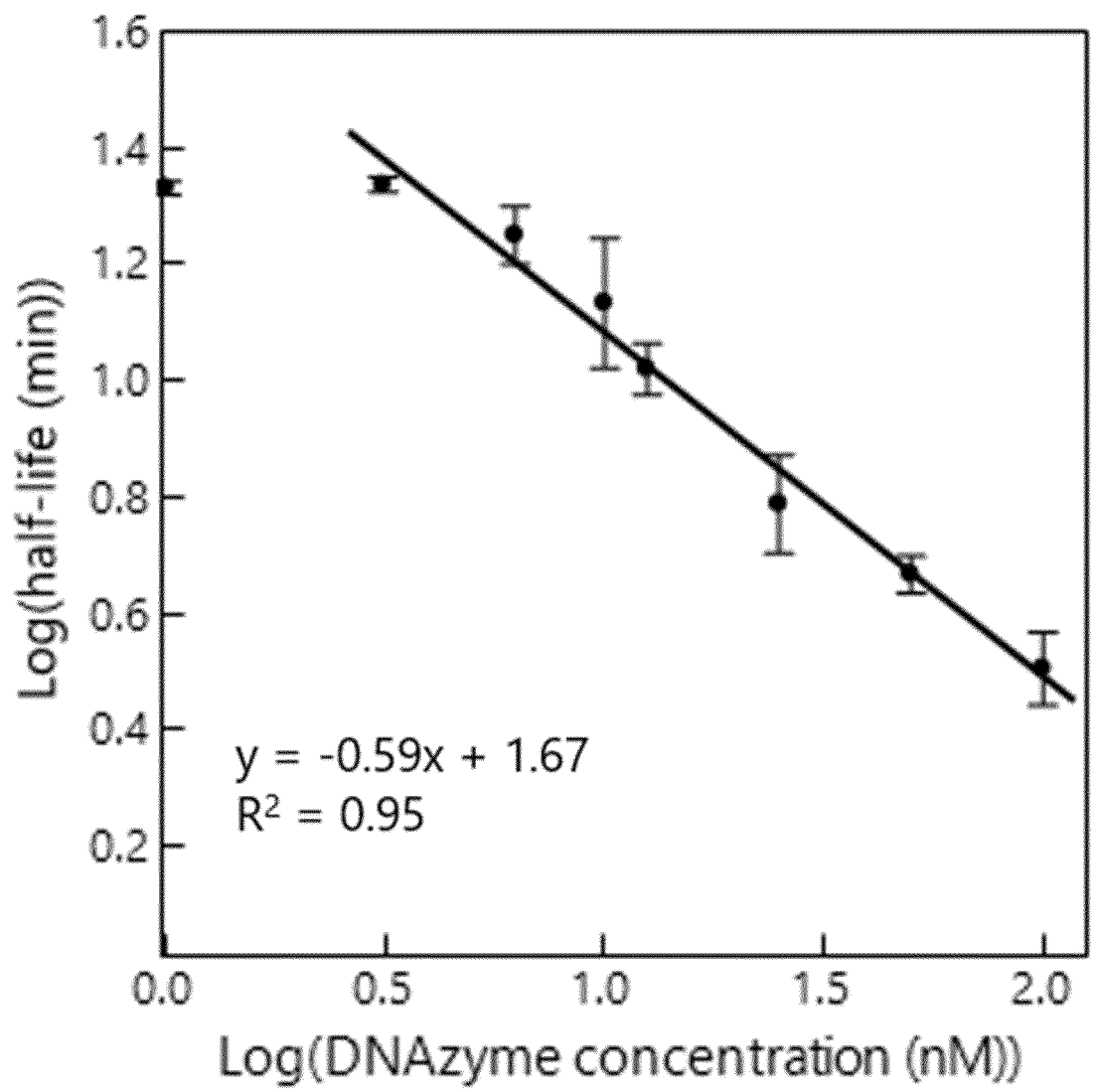
FIG. 12 demonstrates a DNAzyme calibration curve. A linear calibration curve was established by log-log transformation of the half-life and DNAzyme concentration. Error bars represent one standard deviation (n=3).
Figure 13:
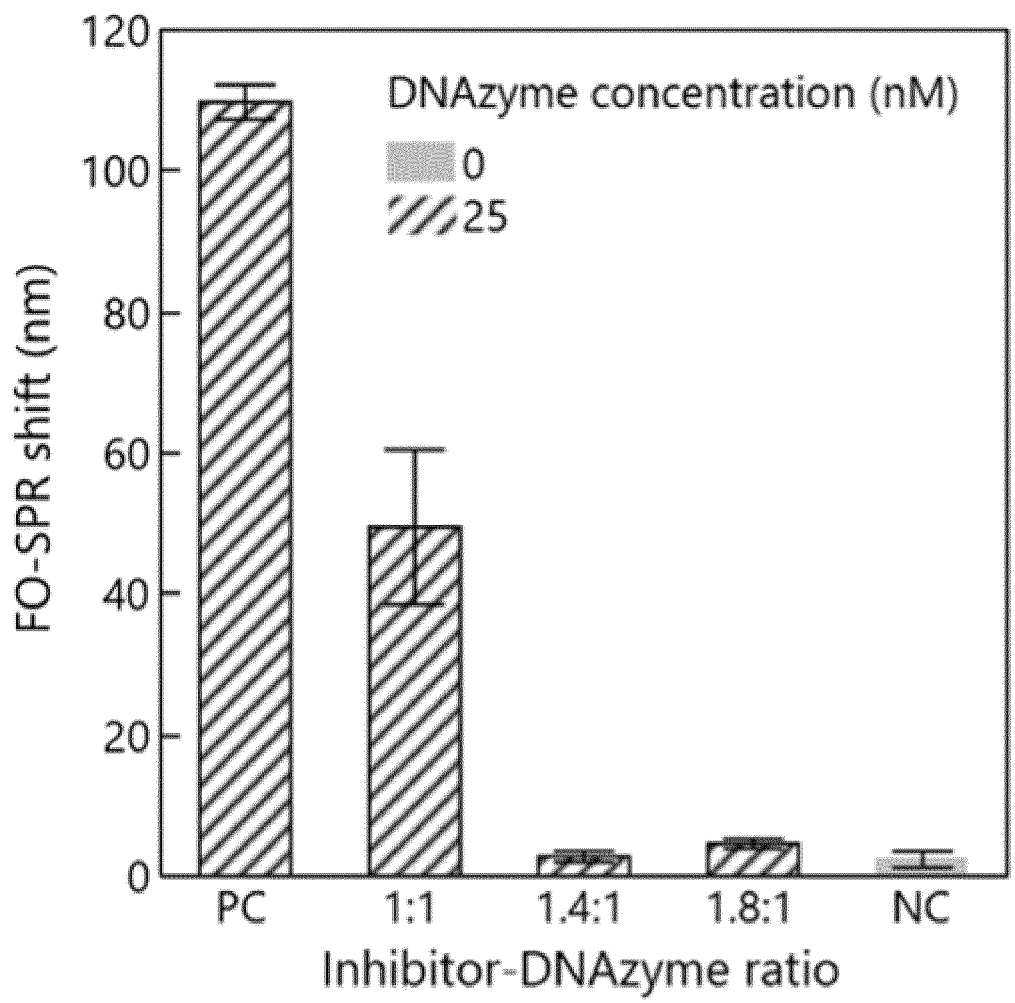
FIG. 13: Optimization of the inhibitor-DNAzyme ratio for DNAzyme inactivation. Positive (PC) and negative control (NC) contained only 25 nM DNAzyme and 200 nM inhibitor respectively. Shaded bars contained 25 nM DNAzyme with increasing amount of inhibitor. Error bars represent one standard deviation (n=3).
Figure 14:
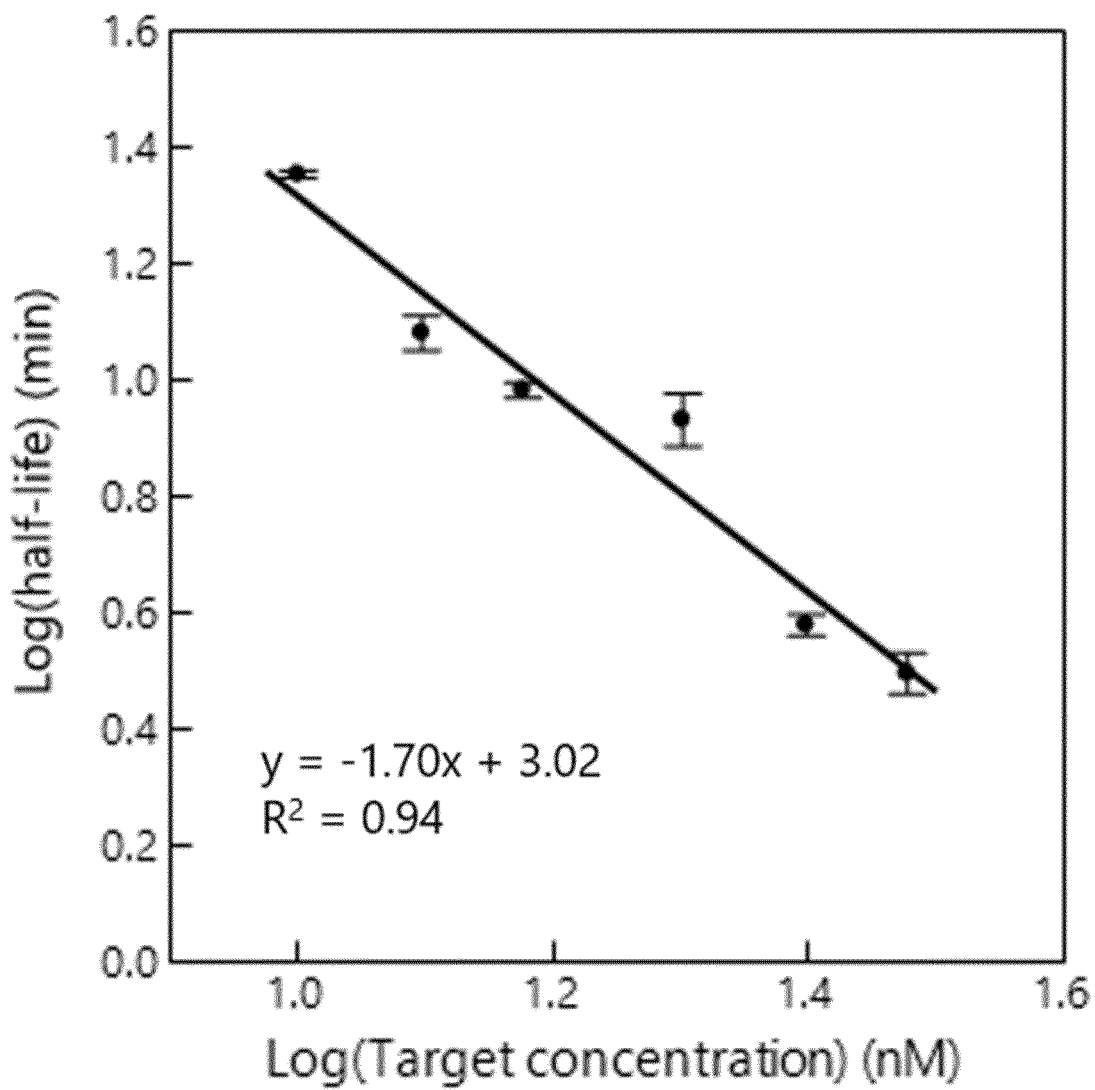
FIG. 14 displays a Log-log linear calibration curve of the half-life values and target concentration from 10-30 nM. Error bars represent one standard deviation (n=3).
Figure 15:
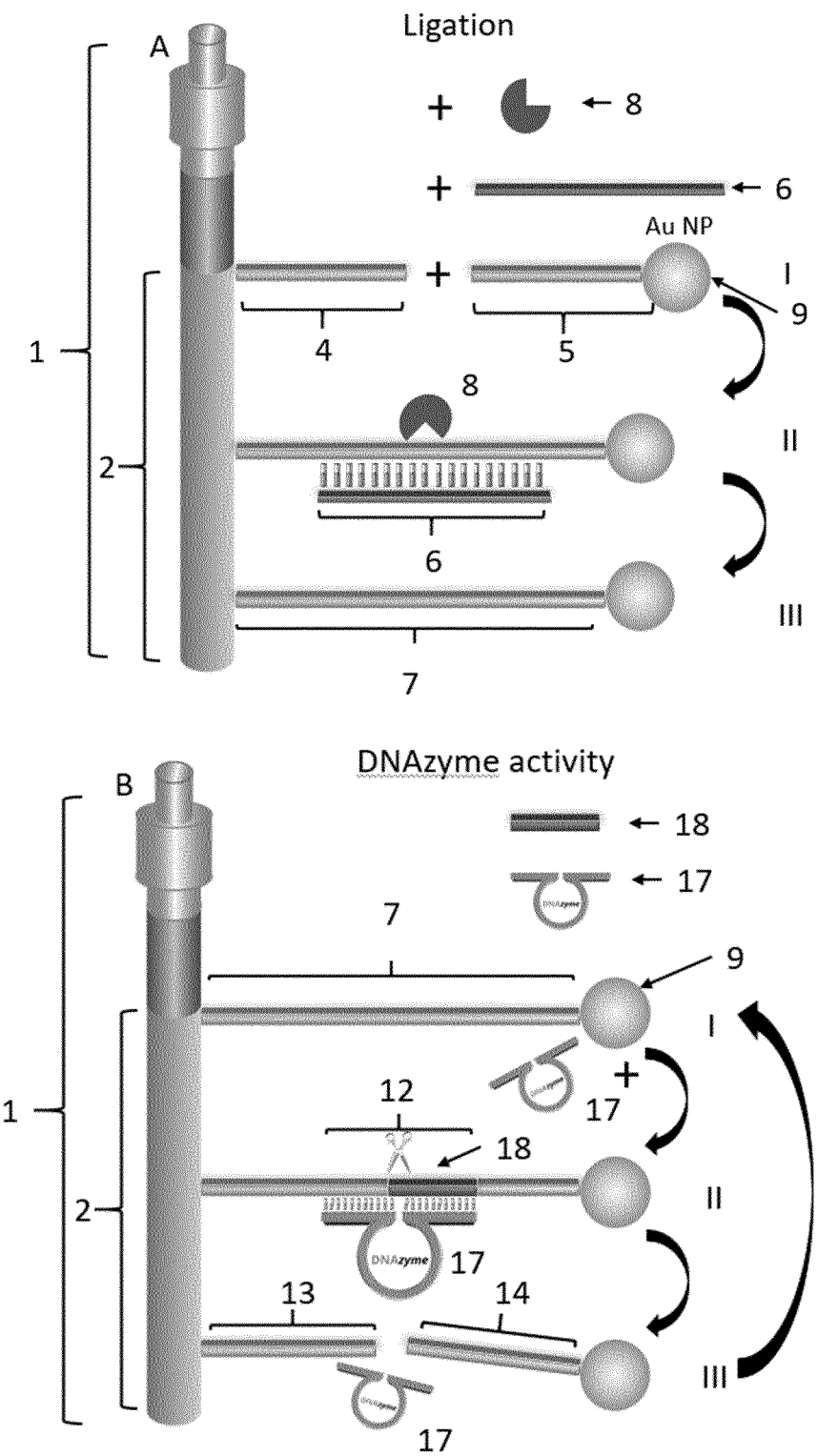
FIG. 15 displays a DNA probe (4) covalently bound to the sensing surface (2) and DNA probe (5) covalently bound to the metallic nanoparticle or a metallic nanoparticle cluster (9) is ligated by ligase (8) with ligation template (6) and the ligation enzyme (3) into single strand DNA probe (7) between the metallic surface (2) and the or metallic nanoparticle cluster (9) whereby the single strand DNA probe (7) incorporates the NAzyme substrate (12) for a selected NAzyme. The ligation zone (18) in between (4) and (5) is situated within the NAzyme substrate (12) hybridized to the NAzyme (17). More particular displays a surface plasmon resonance (SPR)-DNA probe (4) covalently bound to the sensing surface (2) of a SPR sensor tip (1) and a metallic nanoparticle DNA probe (5) covalently bound to the metallic nanoparticle (9) is ligated with ligation template (6) and the ligation enzyme (3) into single strand DNA probe (7) between the sensing surface (2) of the SPR sensor and the metallic nanoparticle (9) whereby the single strand DNA probe (7) incorporates the NAzyme substrate (12) for a selected NAzyme. The ligation zone (18) in between (4) and (5) is situated within the NAzyme substrate (12) hybridized to the NAzyme (17). Yet more particularly a FO-DNA probe (4) covalently bound to the sensing surface (2) of a FO-SPR sensor tip (1) and a gold nanoparticle (AuNP) DNA probe (5) covalently bound to a gold nanoparticle (9) is ligated with ligation template (6) and the ligation enzyme (3) into single strand DNA probe (7) between the sensing surface (2) of the FO-SPR sensor and the gold nanoparticle (9) whereby the single strand DNA probe (7) incorporates the DNAzyme substrate (12) for a selected DNAzyme. The ligation zone (18) in between (4) and (5) is situated within the NAzyme substrate (12) hybridized to the NAzyme (17). The numbers indicating the diverse components are as follows: 1) is the FO-SPR sensor tip, 2) is the sensing surface, 3) is the ligation enzyme, 4) is FO-probe, 5) is AuNP-probe, 6) is ligation template, 7) is ligated FO- and AuNP-probe, 8) zone available for ligation relative to the NAzyme substrate location, 9) is gold nanoparticle, 12) NAzyme substrate, 13) probe remaining on FO-probe after ligation, 14) probe remaining on AuNP after ligation, 17) DNAzyme, 18) Ligation zone.
Figure 16:
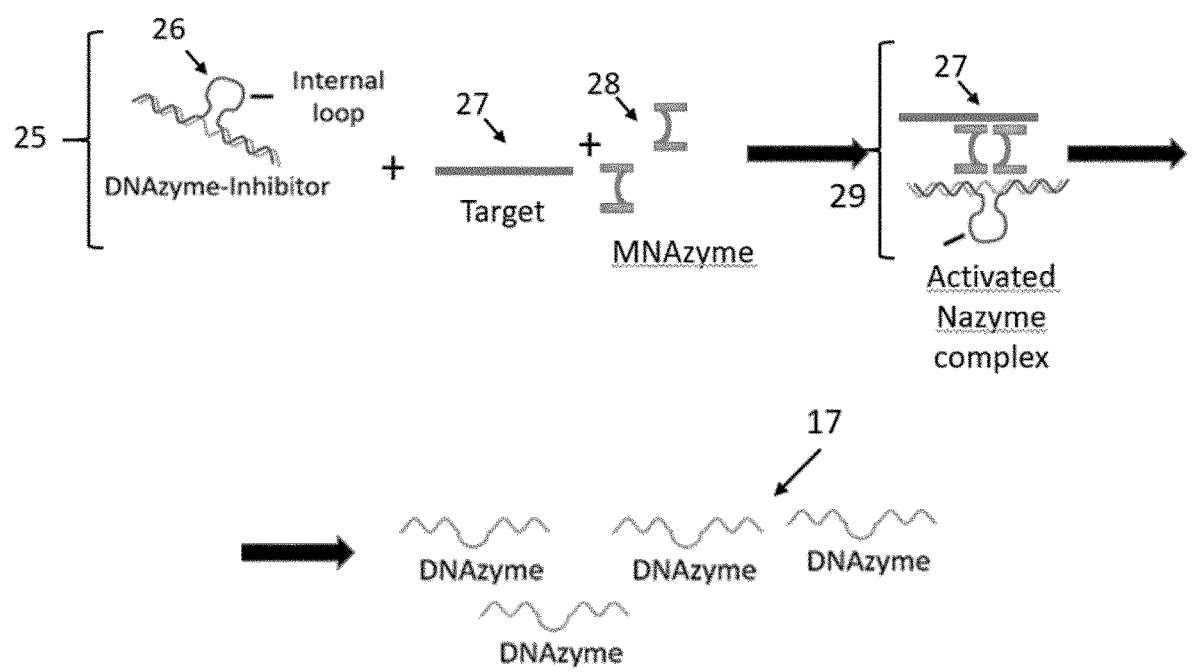
FIG. 16 is a drawing of a scheme that displays DNAzyme activation by target induced MNAzyme activity. A blocked Nazyme (25) is inhibited by a complementary single strand DNA presenting an internal loop (26). An MNAzyme consisting of 2 parts of a whole remains separated until a third (target) single strand DNA combines the three parts through hybridization creating an activated NAzyme complex (29). The activated NAzyme complex (29) cleaves the single strand DNA presenting an internal loop (26) and dehybridizes from the DNAzyme (17) which becomes activated.
Figure 17A:
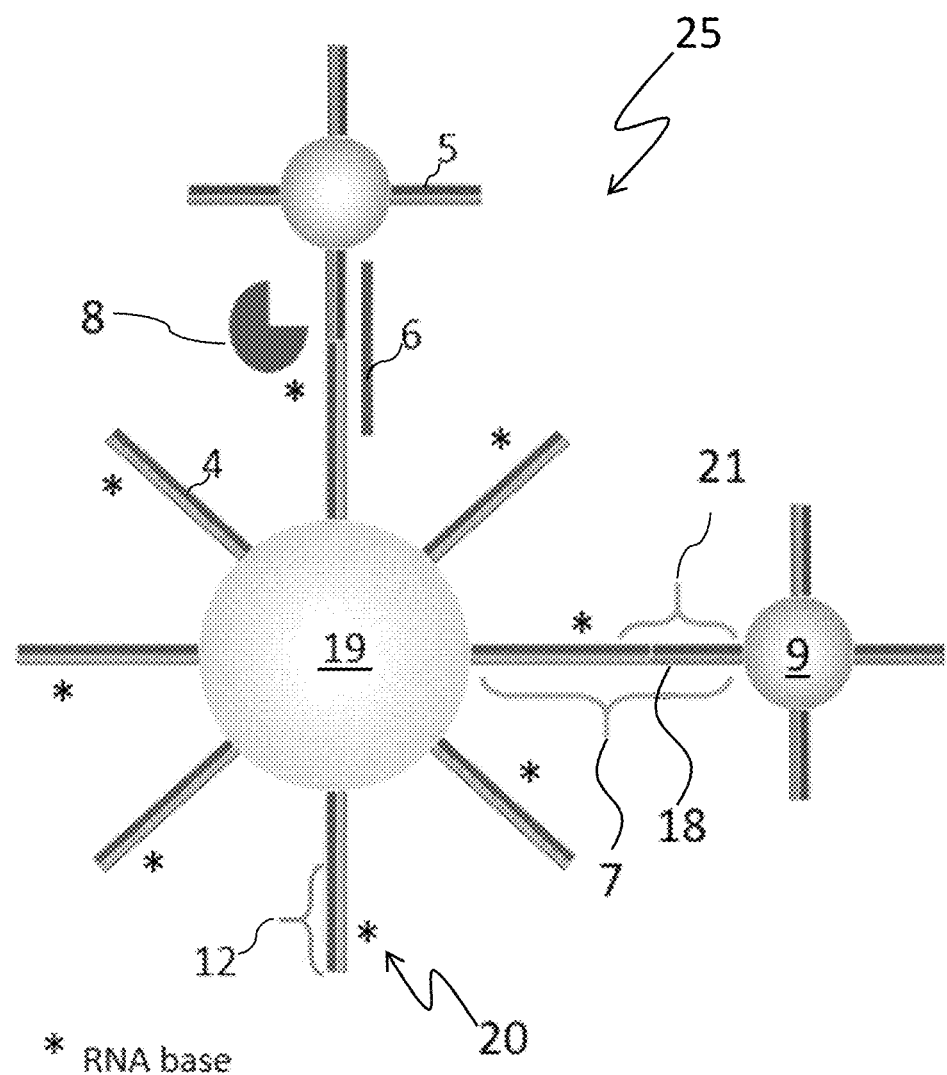
FIG. 17 is that drawing a scheme showing four steps displayed in FIG. 17A to FIG. 17B to FIG. 17C and to FIG. 17D, namely Step 1 NAzyme substrate complex formation, Step 2: Activated NAzyme cleaves Nazyme substrate complex which is eventually after an inhibited NAzyme is activated or a NAzyme is amplified by target, Step 3 FO-SPR hybridization and Step 4 melt analysis.
Figure 17B:
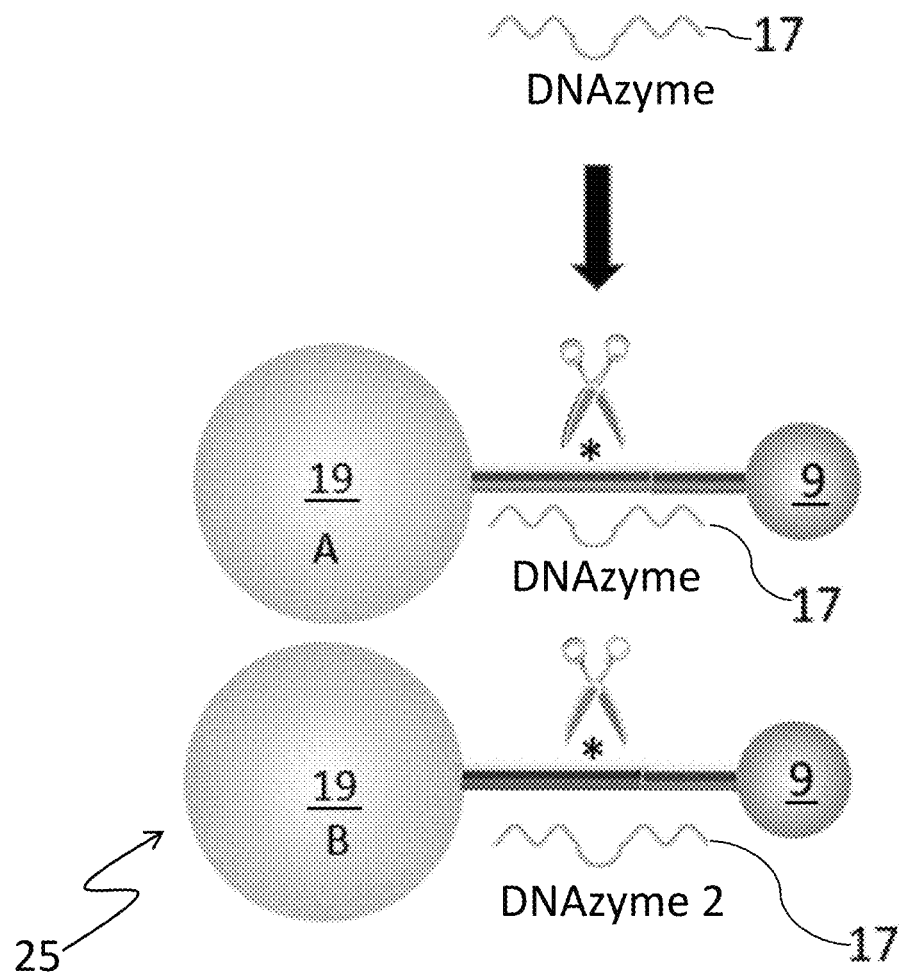
Figure 17C:
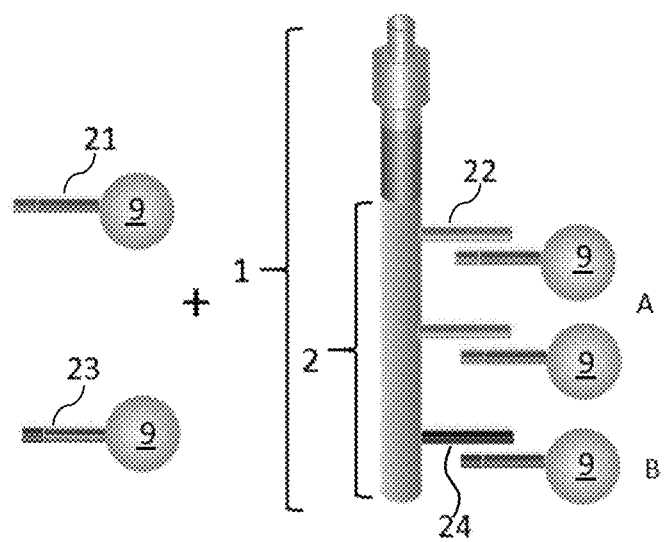
Figure 17D:
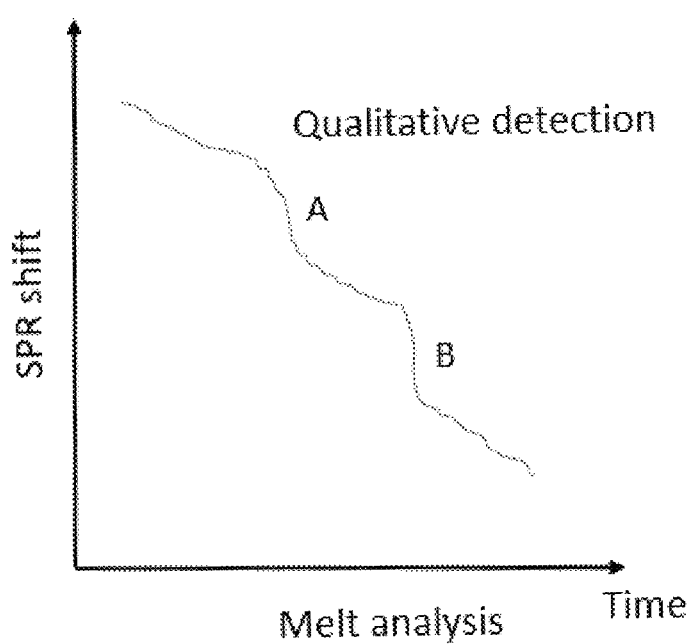

More particular displays a DNA probe (4) covalently bound to the surface of a solid microparticle, microcarrier or microbead (19) and a metallic nanoparticle DNA probe (5) covalently bound to the metallic nanoparticle (9) is ligated with ligation template (6) and the ligation enzyme (8) into single strand DNA probe (7) between separable solid microparticle (19) and the metallic nanoparticle (9) whereby the single strand DNA probe (7) incorporates the NAzyme substrate (12) for a selected NAzyme. The ligation zone (18) in between (4) and (5) is situated within the NAzyme substrate (12) hybridized to the NAzyme (17). Yet more particularly a microparticle-DNA probe (4) covalently bound to the binding surface of a solid separable microparticle (19) and a gold nanoparticle (AuNP) DNA probe (5) covalently bound to a gold nanoparticle (9) is ligated with ligation template (6) and the ligation enzyme (8) into single strand DNA probe (7) between the binding surface of the solid separable microparticle (19) and the gold nanoparticle (9) whereby the single strand DNA probe (7) incorporates the DNAzyme substrate (12) for a selected DNAzyme. The ligation zone (18) in between (4) and (5) is situated within the NAzyme substrate (12) hybridized to the NAzyme (17).

TABLE 1

| Sequence | Name | Length (bp) | 5' Modification | Sequence 5' → 3' | 3' Modification | Note |
|---|---|---|---|---|---|---|
| SEQ ID NO:1 | FO-SPR probe 1 | 31 | 5Phos | CAGCACAACCrGrUCACCAACCGTTTTTTTTT | 3ThioMC3-D | For all FO-probes, bolded region is bound by the DNAzyme |
| SEQ ID NO:2 | FO-SPR probe 2 | 31 | 5Phos | CAGCACAACCrGrUCACCAACCGCATTTTTTT | 3Bio | |
| SEQ ID NO:3 | AuNP-probe 2 | 25 | 5ThioMC6-D | TTTTTTTTTTTGAGGGATTATTGTTA | — | |
| SEQ ID NON | Template 1 | 25 | — | GGTTGTGCTGTAACAATAATCCCTC | — | |
| SEQ ID NO:5 | FO-SPR probe 3 | 33 | 5ThioMC6-D | TTTTTTTTTTTGAGGGATTATAGTATCAGCACAA | — | For all sequences, bolded region is bound by the DNAzyme |
| SEQ ID NO:6 | AuNP-probe 2 | 23 | 5Phos | CCrGrUCACCAACCGTTTTTTTTTT | 3ThioMC3-D | |
| SEQ ID NO:7 | Template 2 | 24 | — | TTGGTGACGGTTGTGCTGATACTA | — | |
| SEQ ID NO:8 | DNAzyme | 35 | — | CGGTTGGTGAGGCTAGCTACAACGAGGTTGTGCTG | — | Underlined region forms the catalytic core. Regions left and right from the catalytic core are called the substrate arms. |
| SEQ ID NO:9 | Inhibitor strand | 52 | — | CAGCGCAACCTCGTTGATCACGCCTCGTCTCCTCCCAGTAGCCTCACCAACC | — | |
| SEQ ID NO:10 | Target | 43 | — | GGTGAGGCTACTGGGAGGAGACGAGGCGTGATCAACGAGGTTG | — | |

REFERENCES TO THIS APPLICATION

1. Knez, K.; Janssen, K. P. F.; Pollet, J.; Spasic, D.; Lammertyn, J. Small 2012, 8 (6), 868-872.
2. Knez, K.; Spasic, D.; Delport, F.; Lammertyn, J. Biosens. Bioelectron. 2015, 67, 394-399.

3. Lu, J.; Van Stappen, T.; Spasic, D.; Delport, F.; Vermeire, S.; Gils, A.; Lammertyn, J. *Biosens. Bioelectron.* 2016, 79, 173-179.
4. Daems, D.; Lu, J.; Delport, F.; Maridn, N.; Orbie, L.; Aernouts, B.; Adriaens, I.; Huybrechts, T.; Saeys, W.; Spasic, D.; Lammertyn, J. *Anal. Chim. Acta* 2017, 950, 1-6.
5. Pollet, J.; Delport, F.; Janssen, K. P. F.; Jans, K.; Maes, G.; Pfeiffer, H.; Wevers, M.; Lammertyn, J. *Biosens. Bioelectron.* 2009, 25 (4), 864-869.
6. Malinský, P.; Slepička, P.; Hnatowicz, V.; Svorčík, V. *Nanoscale Res. Lett.* 2012, 7 (1), 241.
7. Breaker, R. R.; Joyce, G. F. *Chem. Biol.* 1994, 1, 223-229.
8. Santoro, S. W.; Joyce, G. F. *Proc. Nat. Acad. Sci.* 1997, 94 (9), 4262-4266.
9. Bone, S. M.; Lima, N. E.; Todd, A. V. *Biosens. Bioelectron.* 2015, 70, 330-337.
10. Markham, N. R.; Zuker, M. *Nucleic Acids Res.* 2005, 33 (Web Server), W577-W581.
11. Markham, N. R.; Zuker, M. In *Bioinformatics, Volume II. Structure, Function and Applications*, number 453 in *Methods in Molecular Biology*; Keith, J. M., Ed.; Humana Press: Totowa, N.J., 2008; pp 3-31.
12. Yurke, B.; Turberfield, A. J.; Mills, A. P.; Simmel, F. C.; Neumann, J. L. *Nature* 2000, 406 (6796), 605-608.
13. J. Kosman and B. Juskowiak, *Anal. Chim. Acta*, vol. 707, no. 1, pp. 7-17, 2011
14. A. J. Boersma, et al. *Angew. Chemie Int.* Ed., vol. 48, no. 18, pp. 3346-3348, 2009
15. Y. Li and D. Sen, *Nat. Struct. Biol.*, vol. 3, no. 9, pp. 743-747, 1996
16. E. Mokany, S. M. et al. *Journal of the American Chemical Society*, vol. 132, no. 3. pp. 1051-1059, January-2010
17. T. Velyian et al. EP2817421

---

What is claimed is:

1. A NAzyme activity surface plasmon resonance sensor, comprising:
   a first DNA probe covalently connected to a sensing surface; and
   a second DNA probe covalently connected to a nanoparticle or a nanoparticle cluster,
wherein:
   the first DNA probe and the second DNA probe are ligated together to provide a selected single strand DNA probe that is covalently connected to the sensing surface and to the nanoparticle or the nanoparticle cluster; and
   the selected single strand DNA probe comprises a NAzyme substrate and a ligation zone within the NAzyme substrate, whereby the NAzyme activity surface plasmon resonance sensor is adapted to measure DNAzyme activity by NAzyme binding to the selected single strand DNA probe at the NAzyme substrate and cleavage of the selected single strand DNA probe at the ligation zone.

2. The NAzyme activity surface plasmon resonance sensor of claim 1, wherein the NAzyme substrate is a substrate for a selected NAzyme, whereby the NAzyme activity surface plasmon resonance sensor is adapted to measure activity of the selected NAzyme.

3. The NAzyme activity surface plasmon resonance sensor of claim 1, wherein the sensing surface is covered by a gold coating.

4. The NAzyme activity surface plasmon resonance sensor of claim 1, wherein the second DNA probe is covalently connected to a metallic nanoparticle, whereby the selected single strand DNA probe is covalently connected to the sensing surface and to the metallic nanoparticle.

5. A sensor kit comprising:
   a NAzyme activity surface plasmon resonance sensor according to claim 1; and
   a reversible NAzyme inhibitor.

6. The sensor kit of claim 5, wherein the reversible NAzyme inhibitor comprises a NAzyme blocking DNA sequence and a target recognition aptamer.

7. The sensor kit of claim 5, further comprising an inhibitor strand or a NAzyme blocking DNA sequence, the reversible NAzyme inhibitor comprising a NAzyme binding arm and an internal loop for binding of a specific target independent of catalytic activity from the NAzyme binding arm.

8. The sensor kit of claim 7, wherein the specific target is selected from the group consisting of peptides, polypeptides, sugars, proteins, small molecules, nucleotides, and fat groups.

9. The sensor kit of claim 5, wherein the metallic nanoparticle is gold nanoparticle (AuNP).

10. The sensor kit of claim 5, wherein the sensing surface is covered by a gold coating.

11. The sensor kit of claim 5, further comprising a selected NAzyme-substrate SPR-metallic nanoparticle-probe.

12. A fiber optic surface plasmon resonance sensor tip of a sensor for measuring NAzyme activity or for measuring cleaving activity of an enzyme on a DNA substrate, the fiber optic surface plasmon resonance sensor tip comprising:
   a sensing surface;
   a metallic nanoparticle or cluster of metallic nanoparticles; and
   a single strand DNA probe covalently connected to the sensing surface and to the metallic nanoparticle nanoparticle or cluster of metallic nanoparticles, wherein:
the single strand DNA probe comprises a NAzyme substrate and a ligation zone within the NAzyme substrate;
the sensor is adapted to measure an activity of a selected NAzyme when the NAzyme substrate is recognized by the selected NAzyme through hybridization and the metallic nanoparticle or cluster of metallic nanoparticles is released from the sensor by cleavage of the single strand DNA at the ligation zone by the selected NAzyme.

13. The fiber optic surface plasmon resonance sensor tip of claim 12, wherein the sensing surface is covered by a gold coating.

14. The fiber optic surface plasmon resonance sensor tip of claim 12, further comprising a selected NAzyme-substrate surface plasmon resonance (SPR) metallic nanoparticle-probe.

* * * * *

UNITED STATES PATENT AND TRADEMARK OFFICE
CERTIFICATE OF CORRECTION

PATENT NO. : 11,614,403 B2
APPLICATION NO. : 16/645170
DATED : March 28, 2023
INVENTOR(S) : Devin Daems et al.

It is certified that error appears in the above-identified patent and that said Letters Patent is hereby corrected as shown below:

On the Title Page

Item (73), assignee, delete "FOX BIOSYSTEMS NV, Temse (BE)" and insert --FOx BIOSYSTEMS NV, Diepenbeek (BE)--, therefor.

Item (74), attorney, agent, or firm, delete "Dinsmore & Shohl, LLP" and insert --Dinsmore & Shohl LLP--, therefor.

Column 2, item (56), other publications, cite no. 11, delete "Fiber-optick" and insert --Fiber-optic--, therefor.

In the Specification

In Column 20, Line(s) 62, delete "than" and insert --then--, therefor.

In Column 24, Line(s) 6, after "ligation", delete "an" and insert --and--, therefor.

In Column 33, Line(s) 4, delete "Maridn" and insert --Mariën--, therefor.

Signed and Sealed this
Third Day of October, 2023

Katherine Kelly Vidal
*Director of the United States Patent and Trademark Office*